(12) United States Patent
Schecter

(10) Patent No.: US 8,942,828 B1
(45) Date of Patent: Jan. 27, 2015

(54) MINIMALLY INVASIVE CARDIOVASCULAR SUPPORT SYSTEM WITH TRUE HAPTIC COUPLING

(75) Inventor: Stuart O. Schecter, Great Neck, NY (US)

(73) Assignee: Stuart Schecter, LLC, Great Neck, NY (US)

( * ) Notice: Subject to any disclaimer, the term of this patent is extended or adjusted under 35 U.S.C. 154(b) by 253 days.

(21) Appl. No.: 13/447,064

(22) Filed: Apr. 13, 2012

Related U.S. Application Data

(60) Provisional application No. 61/517,073, filed on Apr. 13, 2011.

(51) Int. Cl.
*A61N 1/00* (2006.01)
*A61N 1/05* (2006.01)

(52) U.S. Cl.
CPC .. *A61N 1/05* (2013.01); *A61N 1/056* (2013.01)
USPC ............................ 607/122; 607/119; 607/116

(58) Field of Classification Search
CPC .......... A61N 1/056; A61N 1/05; A61N 1/375
USPC ......................................... 607/122, 119, 116
See application file for complete search history.

(56) References Cited

U.S. PATENT DOCUMENTS

| | | |
|---|---|---|
| 3,184,842 A | 5/1965 | Nicholas |
| 4,019,073 A | 4/1977 | Vishnevsky et al. |
| 4,210,837 A | 7/1980 | Vasiliev et al. |
| 4,432,372 A | 2/1984 | Monroe |

(Continued)

FOREIGN PATENT DOCUMENTS

| | | |
|---|---|---|
| EP | 0970663 A1 | 1/2000 |
| KR | 20110004401 A | 1/2011 |

(Continued)

OTHER PUBLICATIONS

Makoto Shimojo et al., A High-Speed Mesh of Tactile Sensors Fitting Arbitrary Surfaces, IEEE Sensor Journal, vol. 10, No. 4, Apr. 2010.

(Continued)

*Primary Examiner* — Christopher D Koharski
*Assistant Examiner* — Philip Edwards
(74) *Attorney, Agent, or Firm* — Patterson Thuente Pedersen P.A.

(57) ABSTRACT

A family of minimally-invasive surgical (MIS) cardiac interventional tools with tactile feedback based upon cardiac mechanical data and physiologic parameters derived from sensors positioned upon the tools are configurable for optimal placement of an end-effector to provide acute cardiac resuscitation and/or remote cardiovascular intervention for a subject. A haptic interface (e.g., a haptic handle, haptic glove or a simulated haptic heart) provides a clinician with real, not virtual, interaction with the cardiovascular anatomy (including intrathoracic organs) of the subject to optimize end-effector placement. The MIS tools optionally include webbed blade portions for exploration of extracardiac or intrathoracic spaces. The blade portions are initially collapsed but expand into an array of finger-like projections that function as sensors, dilatation and/or dissection tools, pharmacological delivery tools, and/or electrodes for sensing, pacing and defibrillation, and/or as a manual, semi-automatic or fully automatic mechanical support system for cardiac resuscitation and/or for restoring intrathoracic organ function(s).

8 Claims, 8 Drawing Sheets

(56) References Cited

U.S. PATENT DOCUMENTS

| | | | |
|---|---|---|---|
| 4,844,062 A | 7/1989 | Wells | |
| 5,389,865 A | 2/1995 | Jacobus et al. | |
| 5,429,604 A | 7/1995 | Hammersmark et al. | |
| 5,484,433 A | 1/1996 | Taylor et al. | |
| 5,549,650 A | 8/1996 | Bornzin et al. | |
| 5,576,727 A | 11/1996 | Rosenberg et al. | |
| 5,609,607 A | 3/1997 | Hechtenberg et al. | |
| 5,628,777 A | 5/1997 | Moberg et al. | |
| 5,693,074 A | 12/1997 | Ferek Petric | |
| 5,702,438 A * | 12/1997 | Avitall | 607/122 |
| 5,769,640 A | 6/1998 | Jacobus et al. | |
| 5,771,902 A | 6/1998 | Lee et al. | |
| 5,833,623 A | 11/1998 | Mann et al. | |
| 5,836,946 A | 11/1998 | Diaz et al. | |
| 5,843,135 A | 12/1998 | Weijand et al. | |
| 5,844,392 A | 12/1998 | Peurach et al. | |
| 5,916,143 A | 6/1999 | Apple et al. | |
| 5,944,022 A | 8/1999 | Nardella et al. | |
| 5,959,613 A | 9/1999 | Rosenberg et al. | |
| 5,971,931 A | 10/1999 | Raff | |
| 6,059,759 A | 5/2000 | Mottola et al. | |
| 6,070,100 A | 5/2000 | Bakels et al. | |
| 6,077,236 A | 6/2000 | Cunningham | |
| 6,096,004 A | 8/2000 | Meglan et al. | |
| 6,104,158 A | 8/2000 | Jacobus et al. | |
| 6,147,674 A | 11/2000 | Rosenberg et al. | |
| 6,203,432 B1 | 3/2001 | Roberts et al. | |
| 6,278,439 B1 | 8/2001 | Rosenberg et al. | |
| 6,300,936 B1 | 10/2001 | Braun et al. | |
| 6,304,777 B1 | 10/2001 | Ben-Haim et al. | |
| 6,418,346 B1 | 7/2002 | Nelson et al. | |
| 6,424,356 B2 | 7/2002 | Chang et al. | |
| 6,429,849 B1 | 8/2002 | An et al. | |
| 6,442,433 B1 | 8/2002 | Linberg | |
| 6,480,745 B2 | 11/2002 | Nelson et al. | |
| 6,526,984 B1 | 3/2003 | Nilsson et al. | |
| 6,527,683 B2 | 3/2003 | Tolles | |
| 6,572,560 B1 | 6/2003 | Watrous et al. | |
| 6,574,511 B2 | 6/2003 | Lee | |
| 6,622,045 B2 | 9/2003 | Snell et al. | |
| 6,628,988 B2 | 9/2003 | Kramer et al. | |
| 6,641,480 B2 | 11/2003 | Murzanski et al. | |
| 6,685,732 B2 | 2/2004 | Kramer | |
| 6,725,091 B2 | 4/2004 | Dal Molin | |
| 6,740,033 B1 | 5/2004 | Olejniczak et al. | |
| 6,746,972 B1 | 6/2004 | Kim et al. | |
| 6,780,183 B2 | 8/2004 | Jimenez, Jr. et al. | |
| 6,792,308 B2 | 9/2004 | Corbucci | |
| 6,795,732 B2 | 9/2004 | Stadler et al. | |
| 6,801,008 B1 | 10/2004 | Jacobus et al. | |
| 6,804,559 B1 | 10/2004 | Kraus et al. | |
| 6,805,667 B2 | 10/2004 | Christopherson et al. | |
| 6,810,281 B2 | 10/2004 | Brock et al. | |
| 6,816,301 B1 | 11/2004 | Schiller | |
| 6,826,509 B2 | 11/2004 | Crisco, III et al. | |
| 6,837,886 B2 * | 1/2005 | Collins et al. | 606/41 |
| 6,863,943 B2 | 3/2005 | Wang et al. | |
| 6,906,700 B1 | 6/2005 | Armstrong | |
| 7,010,347 B2 | 3/2006 | Schecter | |
| 7,063,671 B2 | 6/2006 | Couvillon, Jr. | |
| 7,065,400 B2 | 6/2006 | Schechter | |
| 7,091,948 B2 | 8/2006 | Chang et al. | |
| 7,101,347 B2 | 9/2006 | Culhane et al. | |
| 7,127,289 B2 | 10/2006 | Yu et al. | |
| 7,139,621 B2 | 11/2006 | Gharsalli | |
| 7,147,633 B2 | 12/2006 | Chee et al. | |
| 7,154,470 B2 | 12/2006 | Tierling | |
| 7,168,042 B2 | 1/2007 | Braun et al. | |
| 7,176,892 B2 | 2/2007 | Kobayashi | |
| 7,183,568 B2 | 2/2007 | Appenzeller et al. | |
| 7,191,191 B2 | 3/2007 | Peurach et al. | |
| 7,199,790 B2 | 4/2007 | Rosenberg et al. | |
| 7,206,633 B2 | 4/2007 | Saba | |
| 7,209,117 B2 | 4/2007 | Rosenberg et al. | |
| 7,218,310 B2 | 5/2007 | Tierling et al. | |
| 7,225,404 B1 | 5/2007 | Zilles et al. | |
| 7,257,447 B2 | 8/2007 | Cates et al. | |
| 7,266,832 B2 | 9/2007 | Miller | |
| 7,316,681 B2 | 1/2008 | Madhani et al. | |
| 7,331,967 B2 | 2/2008 | Lee et al. | |
| 7,333,643 B2 | 2/2008 | Murphy et al. | |
| 7,369,115 B2 | 5/2008 | Cruz-Hernandez et al. | |
| 7,386,365 B2 | 6/2008 | Nixon | |
| 7,426,412 B1 | 9/2008 | Schecter | |
| 7,623,114 B2 | 11/2009 | Rank | |
| 7,639,232 B2 | 12/2009 | Grant et al. | |
| 7,653,436 B2 | 1/2010 | Schecter | |
| 7,656,388 B2 | 2/2010 | Schena et al. | |
| 7,689,283 B1 | 3/2010 | Schecter | |
| 7,701,438 B2 | 4/2010 | Chang et al. | |
| 7,720,529 B1 | 5/2010 | Schecter | |
| 7,725,214 B2 | 5/2010 | Diolaiti | |
| 7,740,627 B2 | 6/2010 | Gammie et al. | |
| 7,751,888 B1 | 7/2010 | Schecter | |
| 7,751,889 B1 | 7/2010 | Schecter | |
| 7,762,985 B2 | 7/2010 | Kabrick et al. | |
| 7,765,333 B2 | 7/2010 | Cruz-Hernandez et al. | |
| 7,770,262 B2 | 8/2010 | Schultz et al. | |
| 7,779,166 B2 | 8/2010 | Grant et al. | |
| 7,780,651 B2 | 8/2010 | Madhani et al. | |
| 7,791,588 B2 | 9/2010 | Tierling et al. | |
| 7,794,455 B2 | 9/2010 | Abboud et al. | |
| 7,805,194 B1 | 9/2010 | Schecter | |
| 7,821,493 B2 | 10/2010 | Tierling et al. | |
| 7,821,498 B2 | 10/2010 | Kramer et al. | |
| 7,843,158 B2 | 11/2010 | Prisco | |
| 7,850,642 B2 | 12/2010 | Moll et al. | |
| 7,865,269 B2 | 1/2011 | Prisco et al. | |
| 7,898,156 B2 | 3/2011 | Wang et al. | |
| 7,924,144 B2 | 4/2011 | Makinen et al. | |
| 7,931,586 B2 | 4/2011 | Brock et al. | |
| 7,942,868 B2 | 5/2011 | Cooper | |
| 7,947,050 B2 | 5/2011 | Lee et al. | |
| 7,947,051 B2 | 5/2011 | Lee et al. | |
| 7,963,288 B2 | 6/2011 | Rosenberg et al. | |
| 7,963,925 B1 | 6/2011 | Schecter | |
| 7,969,288 B2 | 6/2011 | Braun et al. | |
| 7,970,469 B2 | 6/2011 | Schecter | |
| 7,972,298 B2 | 7/2011 | Wallace et al. | |
| 7,974,681 B2 | 7/2011 | Wallace et al. | |
| 7,978,183 B2 | 7/2011 | Rosenberg et al. | |
| 7,979,146 B2 | 7/2011 | Ullrich et al. | |
| 7,982,588 B2 | 7/2011 | Makinen et al. | |
| 7,982,720 B2 | 7/2011 | Rosenberg et al. | |
| 8,000,825 B2 | 8/2011 | Ullrich et al. | |
| 8,003,982 B2 | 8/2011 | Wang et al. | |
| 8,004,229 B2 | 8/2011 | Nowlin et al. | |
| 8,010,180 B2 | 8/2011 | Quaid et al. | |
| 8,014,864 B2 | 9/2011 | Schecter | |
| 8,016,818 B2 | 9/2011 | Ellis et al. | |
| 8,026,798 B2 | 9/2011 | Makinen et al. | |
| 8,032,212 B2 | 10/2011 | Bornzin et al. | |
| 8,039,834 B2 | 10/2011 | Wang et al. | |
| 8,041,413 B2 | 10/2011 | Barbagli et al. | |
| 8,043,351 B2 | 10/2011 | Yon et al. | |
| 8,050,760 B2 | 11/2011 | Cholette | |
| 8,059,105 B2 | 11/2011 | Rosenberg et al. | |
| 8,090,444 B2 | 1/2012 | Min et al. | |
| 8,156,809 B2 | 4/2012 | Tierling et al. | |
| 8,174,373 B2 | 5/2012 | Makinen et al. | |
| 8,209,012 B2 | 6/2012 | Schecter | |
| 8,211,032 B2 | 7/2012 | Schecter et al. | |
| 8,214,039 B1 | 7/2012 | Schecter | |
| 8,292,797 B2 | 10/2012 | Chapman et al. | |
| 2002/0015950 A1 | 2/2002 | Jones et al. | |
| 2002/0026103 A1 | 2/2002 | Norris et al. | |
| 2002/0072784 A1 | 6/2002 | Sheppard et al. | |
| 2002/0120188 A1 | 8/2002 | Brock et al. | |
| 2002/0183738 A1 | 12/2002 | Chee et al. | |
| 2003/0006669 A1 | 1/2003 | Pei et al. | |
| 2003/0083702 A1 | 5/2003 | Stadler et al. | |
| 2003/0187362 A1 | 10/2003 | Murphy et al. | |
| 2003/0216620 A1 | 11/2003 | Jain et al. | |
| 2004/0019285 A1 | 1/2004 | Eigler et al. | |

(56) References Cited

U.S. PATENT DOCUMENTS

| | | |
|---|---|---|
| 2004/0068199 A1 | 4/2004 | Echauz et al. |
| 2004/0111127 A1 | 6/2004 | Gliner |
| 2004/0153128 A1 | 8/2004 | Suresh et al. |
| 2004/0167587 A1 | 8/2004 | Thompson |
| 2004/0172079 A1 | 9/2004 | Chinchoy |
| 2004/0176679 A1 | 9/2004 | Murphy et al. |
| 2004/0176810 A1 | 9/2004 | Stadler et al. |
| 2004/0186465 A1 | 9/2004 | Francischelli et al. |
| 2004/0231100 A1 | 11/2004 | Schultz et al. |
| 2005/0043895 A1 | 2/2005 | Schechter |
| 2005/0059876 A1 | 3/2005 | Krishnan et al. |
| 2005/0113886 A1 | 5/2005 | Fischell et al. |
| 2005/0182447 A1 | 8/2005 | Schecter |
| 2005/0241026 A1 | 10/2005 | Esler et al. |
| 2005/0262676 A1 | 12/2005 | Kim et al. |
| 2005/0280508 A1 | 12/2005 | Mravca et al. |
| 2006/0059997 A1 | 3/2006 | Kim et al. |
| 2006/0083720 A1 | 4/2006 | Fraser et al. |
| 2006/0114088 A1 | 6/2006 | Shachar |
| 2006/0159747 A1 | 7/2006 | Schumacher et al. |
| 2006/0161045 A1 | 7/2006 | Merril et al. |
| 2006/0167529 A1 | 7/2006 | Schecter |
| 2006/0276775 A1 | 12/2006 | Rosenberg et al. |
| 2007/0021977 A1 | 1/2007 | Elsholz |
| 2007/0043338 A1 | 2/2007 | Moll et al. |
| 2007/0103437 A1 | 5/2007 | Rosenberg |
| 2007/0156123 A1 | 7/2007 | Moll et al. |
| 2007/0173861 A1 | 7/2007 | Strommer et al. |
| 2007/0191901 A1 | 8/2007 | Schecter |
| 2007/0197896 A1 | 8/2007 | Moll et al. |
| 2007/0197939 A1 | 8/2007 | Wallace et al. |
| 2007/0233044 A1 | 10/2007 | Wallace et al. |
| 2008/0009750 A1 | 1/2008 | Aeby et al. |
| 2008/0009759 A1 | 1/2008 | Chetham |
| 2008/0009791 A1 | 1/2008 | Cohen et al. |
| 2008/0010705 A1 | 1/2008 | Quaid et al. |
| 2008/0067618 A1 | 3/2008 | Wang et al. |
| 2008/0119871 A1 | 5/2008 | Brock et al. |
| 2008/0218770 A1 | 9/2008 | Moll et al. |
| 2008/0262513 A1 | 10/2008 | Stahler et al. |
| 2008/0275367 A1 | 11/2008 | Barbagli et al. |
| 2008/0288013 A1 | 11/2008 | Schecter |
| 2008/0290040 A1 | 11/2008 | Kane et al. |
| 2008/0303782 A1 | 12/2008 | Grant et al. |
| 2009/0012533 A1 | 1/2009 | Barbagli et al. |
| 2009/0024141 A1 | 1/2009 | Stahler et al. |
| 2009/0030332 A1 | 1/2009 | Schecter |
| 2009/0062602 A1 | 3/2009 | Rosenberg et al. |
| 2009/0066195 A1 | 3/2009 | Wang et al. |
| 2009/0076476 A1* | 3/2009 | Barbagli et al. ............ 604/500 |
| 2009/0123111 A1 | 5/2009 | Udd |
| 2009/0138025 A1 | 5/2009 | Stahler et al. |
| 2009/0167677 A1 | 7/2009 | Kruse et al. |
| 2009/0177095 A1 | 7/2009 | Aeby et al. |
| 2009/0179523 A1 | 7/2009 | Wang et al. |
| 2009/0243997 A1 | 10/2009 | Tierling et al. |
| 2009/0259280 A1* | 10/2009 | Wilkin et al. ............ 607/116 |
| 2009/0299431 A1 | 12/2009 | Schecter |
| 2009/0301196 A1 | 12/2009 | Wang et al. |
| 2009/0312814 A1 | 12/2009 | Schecter et al. |
| 2010/0013761 A1 | 1/2010 | Birnbaum et al. |
| 2010/0017759 A1 | 1/2010 | Birnbaum et al. |
| 2010/0045619 A1 | 2/2010 | Birnbaum et al. |
| 2010/0049060 A1 | 2/2010 | Schecter |
| 2010/0056851 A1 | 3/2010 | Wang et al. |
| 2010/0063478 A1 | 3/2010 | Selkee |
| 2010/0073150 A1 | 3/2010 | Olson et al. |
| 2010/0114115 A1 | 5/2010 | Schlesinger et al. |
| 2010/0117488 A1 | 5/2010 | Wang et al. |
| 2010/0121403 A1 | 5/2010 | Schecter et al. |
| 2010/0123588 A1 | 5/2010 | Cruz Hernandez et al. |
| 2010/0152620 A1 | 6/2010 | Ramsay et al. |
| 2010/0152795 A1 | 6/2010 | Schecter |
| 2010/0152796 A1 | 6/2010 | Schecter |
| 2010/0179587 A1 | 7/2010 | Grant et al. |
| 2010/0228103 A1 | 9/2010 | Schecter |
| 2010/0234913 A1 | 9/2010 | Schecter |
| 2010/0283731 A1 | 11/2010 | Grant et al. |
| 2010/0312129 A1 | 12/2010 | Schecter |
| 2011/0006286 A1 | 1/2011 | Wang et al. |
| 2011/0043454 A1 | 2/2011 | Modarres et al. |
| 2011/0050405 A1 | 3/2011 | Hollis, Jr. et al. |
| 2011/0090070 A1 | 4/2011 | Modarres et al. |
| 2011/0121953 A1 | 5/2011 | Grant et al. |
| 2011/0166513 A1 | 7/2011 | Cohen et al. |
| 2011/0184406 A1 | 7/2011 | Selkee |
| 2011/0193824 A1 | 8/2011 | Modarres et al. |
| 2011/0230896 A1 | 9/2011 | Wallace et al. |
| 2011/0238083 A1 | 9/2011 | Moll et al. |
| 2011/0275947 A1 | 11/2011 | Feldman et al. |
| 2011/0306890 A1 | 12/2011 | Schecter et al. |
| 2012/0265076 A1 | 10/2012 | Schecter |
| 2012/0265083 A1 | 10/2012 | Schecter |

FOREIGN PATENT DOCUMENTS

| | | |
|---|---|---|
| WO | WO2006081132 A2 | 8/2006 |
| WO | WO2006081132 A3 | 11/2007 |
| WO | WO2010129892 A2 | 11/2010 |
| WO | WO2011005814 A1 | 1/2011 |
| WO | WO2011022319 A1 | 2/2011 |
| WO | WO2011046714 A1 | 4/2011 |
| WO | WO2011097356 A1 | 8/2011 |

OTHER PUBLICATIONS

Allison M. Okamura et al., Reality-Based Models for Vibration Feedback in Virtual Environments, IEEE/ ASME Transactions on Mechatronics, vol. 6, No. 3, Sep. 2001.

Office Action issued in related U.S. Appl. No. 11/746,752, Mailed Apr. 5, 2010.

Farrokh Janabi-Sharifi et al., Discrete-Time Adaptive Windowing for Velocity Estimation, IEEE/ASME Transactions on Control Systems Technology, vol. 8, No. 6, Nov. 2000.

Young Qin et al., Microfibre-nanowire Hybrid Structure for Energy Scavenging, School of Materials Science and Engineering, Georgia Institute of Technology, Atlanta, Georgia, USA, vol. 451, Feb. 2008.

S. Stramigioli et al., A Novel Theory for Sample Data System Passivity, IEEE/RSJ, International Conference of Intelligent Robots and Systems, EPFL, Lausanne, Switzerland, Oct. 2002.

Honjie Leng et al., Development of a Novel Deformation-Based Tissue Softness Sensor, IEEE Sensors Journal, vol. 9, No. 5, May 2009.

J. E. Colgate et al., Factors Affecting the Z-Width of a Haptic Display, IEEE, Department of Mechanical Engineering, Northwestern University, 2145 Sheridan Rd., Evanston, Illinois, 1994.

J. E. Colgate et al., Passivity of a Class of Sampled-Data Systems: Application to Haptic Interfaces, IEEE, Department of Mechanical Engineering, Northwestern University, Evanston, IL, Journal of Robotic Systems, John Wiley & Sons Inc, 1997.

Dipen C. Shah et al., Area Under the Real-Time Contact Force Curve (Force-Time Integral) Predicts Radiofrequency Lesion Size in an In Vitro Contractile Model, Journal of Cardiovascular Electrophysiology, vol. No. 10, pp. 1-5, 2010.

Office Action issued in the related U.S. Appl. No. 11/686,602 mailed Jun. 24, 2010.

Excerpts, Heart Rhythm, vol. 2, No. 5, May Supplement, 2005 including Schecter S et al. The Effects of Atrial Flutter on Left Ventricular Rotation: A Tissue Doppler Study. Heart Rhythm Society 2005; 2(1S): S134.

Dissertation of Katherine Julianne Kuchenbecker, Characterizing and Controlling the High Frequency Dynamics of Haptic Devices. PhD Thesis Stanford University Department of Mechanical Engineering. 2006.

Giovanni B. Perego et al. "Simultaneous vs. sequesntial biventricular pacing in dilated cardiomyopathy . . . ", The European Journal of Heart Failure, 5, 2003, pp. 305-313.

Carlo Pappone et al."Cardiac Contractility Modulation by Electric Currents Applied During the Refractory Period in Patiens . . . ",The American Journal of Cardiology, V.90, Dec. 2002.

(56) References Cited

OTHER PUBLICATIONS

P. Ritter et ai."Determination of the optimal atrioventricular delay in DOD pacing, Comparison between echo and peak endocardial measurements", Europace, 1999, 1, pp. 126-130.
Jaroslav Meluzin et ai."A fast and simple echacardiographic method of determination of the optimal atrioventricular delay in patients after . . . " Pace, Jan. 2004,vol. 27.
Ric Willems et al. "Nonexcitatory stimulation as a novel treatment for heart failure: cause for excitement?" European Heart Journal, 2004, 25, pp. 626-628.
James D. Thomas et al. "Digital Echocardiography 2002: Now is the Time" Journal of the American Society of Echocardiography, Aug. 2002.
C-M Yu et al."High prevalence of left ventricular systolic and diastolic asynchrony in patients with confestive heart failure and normal QRS duration" Heart, 2003;89,pp. 54-60.
Carlo Pappone et al."First Human Chronic Experience With Cardiac Contractility Modulation by Nonexcitatory . . . " Journal of Cardiovascular Electrophysiology, vol. 15, 4, 2004.
Dipla, K. et ai."The Sarcoplasmic Reticulum and the Na+/Ca2+ Exchanger Both Contribute to theCa 2+ Transient of Failing Human Ventricular . . . ", Circulation Research, 1999;84.
Padeletti et al."Digital Technology for Cardiac Pacing" The American Journal of Cardiology, vol. 95, Feb. 15, 2005, pp. 479-482.
Harvey Feigenbaum "Digital Echocardiography", Excerpta Medica, Inc., 2000, 2G-3G.
Burknoff et al. "Electric Currents Applied During rhe Refractory Period Can Modulate Cardiac Cotnractility in Vitro and In Vivo", Heart Failure Previews, 6, 2001, pp. 27-34.
PCT Search Report from International Application No. PCT/US06/01946; search report completed Apr. 27, 2007 and mailed Aug. 15, 2007.
Office Action issued in a corresponding U.S. Appl. No. 11/848,346, Dec. 22, 2010.
McMahan et al, Tool Contact Acceleration Feedback for Telerobotic Surgery, IEEE Transactions on Haptics, vol. 4, No. 3, p. 210-220, Jul.-Sep. 2011.
Zhong Y et. al. An electromechanical based deformable model for soft tissue simulation. Artificial Intelligence in Medicine. Nov. 2009; vol. 47, 3, pp. 275-288.
Controlling a Heart Simulator with CompactRIO and LabVIEW, http://sine.ni.com/cs/app/doc/p/id/cs-13021, as accessed on Feb. 13, 2013.
Chubb EC et al. ShiverPaD: A Glass Haptic Surface That Produces Shear Force on a Bare Finger. IEEE Transactions on Haptics 2010, vol. 3, No. 3, pp. 189-198.
Gleeson BT et al. Perception of Direction for Applied Tangential Skin Displacement: Effects of Speed, Displacement, and Repetition. IEEE Transactions on Haptics 2010, vol. 3, No. 3 pp. 177-188.
Mafi R, et. al. A parallel Computing Platform for Real-Time Haptic Interaction with Deformable Bodies. IEEE Transactions on Haptics 2010, vol. 3, No. 3. p. 211-223.
Frisoli A. et al. Kinematic Design of a Two Contact Points Haptic Interface for the Thumb and Index Fingers of the Hand. ASME J Mechanical Design, vol. 129, pp. 520-529, 2007.
Proctor RW et al. Implications of Compatibility and Cuing Effects for Multimodal Interfaces. Proc. Int'l Conf. Human-Computer Interaction, vol. 11, 2005.
Easton RD et. al. Transfer between Vision and Haptics: Memory for 2D Patterns and 3D Objects. Psychonomic Bull. and Rev., vol. 4, pp. 322-325, 1997.
Ahmaniemi T, et al. Design of Dynamic Vibrotactile Textures. IEEE Transactions on Haptics, vol. 3, No. 4. p. 245-256, Oct.-Dec. 2010.
Gleeson BT, et al. Design of a Fingertip-Mounted Tactile Display with Tangential Skin Displacement Feedback. IEEE Transactions on Haptics, vol. 3, No. 4. p. 297-298, Oct.-Dec. 2010.
Ikeda A. et al., Electrogram Prameters (Injury current, amplitude, dV/dt) and Impedance are poor predictors of electrode-tissue contact force for Radiofrequency Ablation. Heart Rhythm Society, May 2008, Abstract 4570, PO5-41.
Burdea, GC., Force and Touch Feedback for Virtual Reality. New York: Wiley Interscience, 1996, Abstract.
Nguyen, CTC, IEEE Spectrum Dec. 2009.
Hannaford B. et al. Stable Control of Haptics. In Touch in Virtual Environments: Proceedings USC Workshop on Haptic Interfaces, edited by Margret McLaughlin. Upper Saddle River, JN; Prentice Hall, 2001.
Abbott JJ, Okamura AM, Effects of Position Quantization and Sampling Rate on Virtual Wall Passivity, IEEE Transactions on Robotics 12:5 (2005), 952-964.
Salcudean SE, and Vlaar TD, On the Emulation of Stiff Walls and Static Friction with a Magneticaly Levitated Input/Output Device. 1996.
Immersion, Touchsense Tactile Feedback, http://www.immersion.com/products/touchsense-tactile-feedback/index.html, as accessed on Feb. 13, 2013.
DuraAct™ Piezoelectric Patch Transducers for Industry and Research, http://www.pi-usa.us/pdf/PI_Catalog_DuraAct_Piezo_Patch_Transducer_Piezo_Composite_C1.pdf, as accessed on Feb. 13, 2013.
Otaduy MA., Haptic Rendering; Foundations, Algorithms and Applications. A.K. Peters Ltd. 2008. p. 138-147, 440.
Extending the Hands of the Endoscopic Surgeon, http://actu.epfl.ch/news/extending-the-hands-of-the-endoscopic-surgeon/, Feb. 4, 2012.
Biosense completes patient enrollment in SMART-AF trial, Medical Device Network, Jan. 13, 2012.
Kawai M., and Yoshikawa T., Haptic Display of Movable Virtual Object with Interface Device Capable of Continuous-Time Impedance Display by Analog Circuit. In IEEE International Conference on Robotics and Automation, pp. 229-234, Washington, DC: IEEE Computer Society 2002.
Bracke, F., Neth Heart J 2008;16(Suppl1): S28-S31.
Coyne KS, Paramore C, Grandy S, Mercader M, Reynolds MR, Zimetbaum P. Assessing the direct costs of treating nonvalvular arterial fibrillation in the United States. *Value Health*, 2006;9:348-356. (PubMed).
Kozak LJ, Lees KA, DeFrances CJ. National Hospital Discharge Survey: 2003 Annual summary with detailed diagnosis and procedure data. *Vital Health Stat*. 2006:1-206.
Go AS, Hylek EM, Phillips KA, Chang Y, Henault LE, Selby JV, Singer DE. Prevalence of diagnosed atrial fibrillation in adults: National implications for rhythm management and stroke prevention. The anticoagulation and risk factors in atrial fibrillation (ATRIA) study. *JAMA* 2001;285:2370-2375.
Miyasaka Y, Barnes ME, Gersh BJ, Cha SS, Bailey KR, Abhayaratna WPS JB, Tsang TSM. Secular trends in incidence of atrial fibrillation in Olmstead County, Minnesota, 1980 to 2000, and implications on the projections for future prevalence. *Circulation*, 2006;114:119-124.
Wattigney WA, Mensah GA, Croft JG. Increasing trends in hospitalization for atrial fibrillation in the United States, 1985 through 1999. *Circulation*. 2003;108:711-716.
Bentkover JD, Stewart EJ, Ignaszewski A, Lepage S, Liu P, Cooper J. *Int J. Cardiol*. Mar. 2003;88(1):33-41. New Technologies and potential cost savings related to morbidity and mortality reduction in Class II/IV heart failure patients in Canada.
Ho KK, Pinsky JL, Kannel WB, Levy D. *J Am Coll Cardiol*. Oct. 1993;22(4 Suppl A):6A-13A. The epidemiology of heart failure: the Framingham Study.
http://www.intertechnology.com/Trans_Tek/TransTek_Series_100.html, as accessed on Feb. 11, 2013.
Tavakoli M. et al. Haptics for Teleoperated Surgical Robotic Systems. pp. 13-30. *World Scientific Publishing Company* 2007.
V Dambrauskaite, et al. "The Evaluation of Pulmonary Hypertension Using Right Ventricular Myocardial Isovolumic Relaxation Time", *J. Am. Soc. Echo*. 2005, 18:1113-20.
P. Caso, et al. "Association between myocardial right ventricular relaxation time and pulmonary atrial pressure in chronic obstructive lung disease analysis by Pulsed Doppler tissue imaging". *J. Am. Echo*. 2001, 14:970-77.
Guido Dehnhardt, Björn Mauck & Horst Bleckmann. *Nature* 394, 235-236 (Jul. 16, 1998) | doi:10.1038/28303.

(56) References Cited

OTHER PUBLICATIONS

Ansalone et al., *JACC* 2002.
Bordacher et al., *JACC* 2004; Dec. 7.
Sogaard, *J. Am Coll Cardiol*, 2002. 40: p. 723-720.
Van Gelder, Berry M., Bracke, Frank A., Meijer, Albert, Lakerveld, Lex JM, Pijls, Nico HJ, "Effect of optimiaing the VV interval on left ventricular contractility in cardiac resynchronization therapy." *Am J Cardiol*, 2004. 93: p. 1500-1503.
Villard E, Dubosscq-Bidot L, Charron P, et al. *Fur Heart J* 2005; 26:795-803.
Daruwala RS, Rudra A, Ostrer H, et al., "A versatile statistical analysis algorithm to detect genome copy number variation:" *Proceedings of the National Academy of Sciences of the United States of America*, Nov. 16, 2004; 101 (46): 16292-7.
Breast Cancer Risk Assessment Tool, http://www.cancer.gov/bcrisktool/, as accessed on Feb. 11, 2013.
Gail Model and NSABP Model, http://www.halls.md/breast/riskcom.htm, as accessed on Feb. 11, 2013.
Selker et al., Patient specific predictions of outcomes in myocardial infarction for real-time emergency use: a thrombolytic predictive instrument. *Ann Intern Med* 1997; 127: 538-56.
Zhang Q. et al., "Assessment of the Effect of Cardiac Resynchronization Therapy on Intraventricular Mechanical Sychronicity be Regional Volumetric Changes." *Am J Cardiol* 2005; 95: 126-129.
Saxon LA, Ellenbogen KA. "Resynchronization Therapy for the Treatment of Heart Failure." *Circulation* 2003; 108: 1044.
Santomauro M et al. "Left ventricular pacing in patients with heart failure: evaluation study with Fourier analysis of radionuclide venticulography." *Ital Heart J* 2004; 5 (12): 906-911.
EUROPA—Press Release—Digital Agenda: European robots helping to perform safer, quicker brain surgery, Nov. 28, 2011.
U.S. Appl. No. 60/634,165, filed Dec. 8, 2004.
Sinnamon LJ, Saad MM, Bowman RM, Gregg JM. "Exploring grain size as a cause for "dead-Layer" effects in thin film capacitors." *Appl. Phys. Lett.* 2002. 81, 703-705.
Sai N. Kolpak AM, Rappe AM. "Ferroelectricity in ultra-thin perovskite films." *Phys. Rev.* 2005. B 72, 020101R.
Shiyou Xu et al 2006 Nanotechnology 17 4497-4501, doi:10.1088/0957-4484/17/17/036.
Nanosprings: Helical Piexoelectric Nanostruxtures Could be Actuators & Transducers in Future Nanosystems, Georgia Tech Research News, http://gtresearchnews.gatech.edu/newsrelease/nanosprings.htm, Oct. 16, 2003.
Cardon nanotube, http://en.wikipedia.org/wiki/carbon_nanotubes, as accessed on Feb. 11, 2013.
Nanotubes-101 Presentation, http://www.cheaptubesinc.com/Carbon-Nanotubes-101.htm, as accessed on Feb. 11, 2013.
Yang, S., Researchers create first ever integrated silicon circuit with nanotube transistors, http://www.berkeley.edu/news/media/releases/2004/01/05_nano.shtml, Jan. 5, 2004.
Philip G. Collins and Phaedon Avouris (2000), Nanotubes for Electronics—*Scientific American* Dec. 2000, 62-69.
Wittkampf FHM et al. "LocalLisa, New Technique for Real Time 2 Dimensional Localization of Regular Intracardiac Electrodes." *Circulation* 1999; 99: 1312-1317.
Packer DL, "Three-Dimensional Mapping of Interventical Electrophysiology: Techniques and Technology." Journal of Cardiovascular Electrophysiology 2005; vol. 16, No. 10, 1110-1117.
Packer DL, "Evolution and mapping and anatomic imaging of cardiac arrhythmias." J Cardiovasc Electrophysiol 2004; 15: 839-854.
Gruner, G., "Carbon Nanotube Films for Transparent and Plastic Electronics." *Journal of Materials Chemistry* 2006, vol. 16, No. 35, pp. 3533-3539.
Gruner, G., "Carbon Nanotube Transistors for Biosensing Applications." *Analytical and Bioanaoytical Chemistry* 2006. vol. 384, pp. 322-335.
Ou, Fung Suong; *Applied Physics Letters* Dec. 2006.
http://bios.ewi.utwente.nl/, as accessed on Feb. 11, 2013.
http://www.mic.dtu.dk/, as accessed on Feb. 11, 2013.
http://www.eng.monash.edu.au/mnrl, as accessed on Feb. 13, 2013.
http://www.appchem.t.u-tokyo.ac.jp/index_e.html, as accessed on Feb. 13, 2013.
http://biomems.uwaterloo.ca/index.html, as accessed on Feb. 11, 2013.
Hocini M, Sanders P, Jais P et al. "Techniques for Curative Treatment of Atrial Fibrillation." *Journal of Cardiovascular Electrophysiology*, vol. 15, No. 12, Dec. 2004, p. 1467.
Oral H, Pappone C, Chugh A. "Circumferential Pulmonary Vein Ablation for Chronic Atrial Fibrillation." *NEJM* 354:9, Mar. 2, 2006, p. 934.
Nademmanee K, Mckenzie J, Koar E, et al. "A New Approach for Catheter Ablation of Atrial Fibrillation: Mapping of the Electrophysiologic Substrate." *JACC* vol. 43, No. 11, 2004. p. 2044.
Gonzalez MD, Otomo K, Shah N. "Transeptal Left Heart Catheterization for Cardiac Ablation Procedures." *J Interventional Cardiac Electrophysiology* 2001. 5, 89-95.
Pappone C, Santinelli V. "The Who, What, Why and How-to Guide for Circumferential Pulmonary Vein Ablation." *J Cardiovascular Electrophysiology* 2004. vol. 15, 1226-1230.
*Circulation*. 2001;104:2118.
Schecter et al. "Guiding Catheters with Side Holes Relieve Pressure Damping and Improve Coronary Blood Flow: Assessment with the Doppler Flowire." *Circulation* 1994; 90: 4, Part 2: 1-164.
Kaneko M, Kanayama N, Tsuji T. "Active Antenna for Contact Sensing." *IEEE Transactions on Robotics and Automation*, vol. 14, No. 2, Apr. 1998. 278-291.
Neimark MA, Andermann JL, Hopfield JJ, Moore CI. "Vibrissa Resonance as a Transduction Mechanism for Tactile Encoding." *J Neurosci*, Jul. 23, 2003. 23(16): 6499-6509.
Hartmann MJ, Johnson NJ, Towal RB, Assad C. "Mechanical Characteristics of Rat Vibrissae: Resonant Frequencies and Damping in Isolated Whiskers and in the Awake Behaving Animal." *J Neurosci*, Jul. 23, 2003. 23(16): 6510-6519.
Krupa DJ, Matell MS, Brisben AJ, Oliveira LM, Nicolelis MAL. "Behavorial Properties of the Trigeminal Somatosensory System in Rats Performing Whicker-Dependent Tactile Discriminations." *J Neurosci*, Aug. 1, 2001, 21(15): 5752-5763.
Solomon JH, Hartmann MJ. "Robotic whiskers used to sense features." *Nature* 2006, vol. 443, 525.
Hsu, JWR et al. "Directed spatial organization of zinc oxide nanorods." *Nano Lett.* 5, 83-86 (2005).
Yoshida N et al. "Validation of Transthoracic Tissue Doppler Assessment of Left Atrial Appendage Function." *J Am Soc Echocardiography* 2007; 20: 521-526.
Dubin et al. "Carbon nanotube Fibers are Compatible With Mammalian Cells and Neurons." *IEEE Transactions on Nanobioscience*, vol. 7, No. 1, Mar. 2008.
Berkelmann PJ, Whitcomb L, Taylor et al. A miniature microsurgical instrument tip force sensor for enhanced force feedback during robot-assisted manipulation. *IEEE Transactions on Robotics and Automation 2003*, 19 (5), 917-922.
Ezhilvalavan S. et al. *J. Phys* 2006. Conf. Ser. 34 979-984.
Stampfer, D.; Jungen, A.; Hierold, C. Sensors, 2004. *Proceedings of IEEE*. Volume, Issue, Oct. 24-27, 2004, pp. 1056-1059 vol. 2.
Singh et al. *Nanotechnology* 2007, 18 475501, abstract.
Hwang, J.D.; Williams, M.D.; Niemeyer, G. Proceedings. 12th International Symposium on Haptic Interfaces for Virtual Environment and Teleoperator Systems, 2004. Haptics apos; 04 Volume, Issue, Mar. 27-28, 2004 pp. 24-31.
Sharifi F, Hayward V, Chen CJ. "Discrete-Time Adaptive Windowing for Velocity Estimation." *IEEE Transactions on Control Systems Technology* 8:6 (2000), 1003-1009.
Rougeron, M. et al. "A Control Approach for Real Time Human Grasp Simulation with Deformable Fingertips." *Intelligent Robots and Systems*, 2006 IEEE/RSJ International Conference Oct. 9-15, 2006 pp. 4634-4640.
Demersseman R et al. "Magnetorhelogical Brake for Haptic Rendering Haptics: Perception, Devices and Scenarios." 6th International Conference, Eurohaptics 2008, Madrid, Spain, Jun. 2008 Proceedings, pp. 940-945.
Khuri-Yakub et al. "Next-Gen Ultrasound." IEEE Spectrum, vol. 46, No. 5, p. 44-54, May 2009.

(56) References Cited

OTHER PUBLICATIONS

Campion G, and Hayward V. "Fundamental Limits in the Rendering of Virtual Haptic Textures." In Proc of the World Haptics Conference. pp. 263-270. Washington DC. IEEE Computer Society 2005.

McNeely et al. "Six Degree of Freedom Haptic Rendering using Voxel Sampling." In Proceedings of SIGGRAOH 99, Computer Graphics Proceedings, Annual Conference Series, Edited by Alyn Rockwood. pp. 401-408. Reading, MA: Addison Wesley Longman 1999.

Moreau JJ, and Jean M. "Numerical Treatment of Contact and Friction: The Contact Dynamics Method." Engineering Systems Design and analysis 4 (1996), 201-208.

Chuang J et al. Embeddable wireless strain sensor based on resonant RF carivites. Rev. Sci. Instrum., vol. 76, No. 9, p. 094703, 2005.

Rizzoli V, et al. A New Wireless Displacement Sensor Based on Reverse Design of Microwave and Millimeter-Wave antenna Array. IEEE Sensors Journal, vol. 9, No. 11, Nov. 2009. p. 1557.

Pulmonary Vein Stenosis Complicating Ablation for Atrial Fibrillation: Clinical Spectrum and Interventional Considerations. David R. Holmes, JrJ Am Coll Cardiol Intv, 2009; 2:267-276.

Pulmonary Vein Anatomy in Patients Undergoing Catheter Ablation of Atrial Fibrillation: Lessons Learned by Use of Magnetic Resonance Imaging. Kato R et al. Circulation. 2003; 107: 2004-2010.

Incidence and Predictors of Pulmonary Vein Stenosis Following Catheter Ablation of Atrial Fibrillation using the Anatomic Pulmnoary Vein Ablation Approach: Results from Paired Magnetic Resonance Imaging. Dong J et al. J Cardiovasc Electrophysiol 2005, vol. 16, pp. 845-852.

Dill T et al. Circulation 2003;107, 845-850.

Sorgente, A. et al. Europace (2011) 13 (2): 205-212.

Tomotsugu T et al. J Am Coll Cardiol, 2003; 41:1243-1250.

Robbins IM, Colvin EV, Doyle TP, et al. Pulmonary vein stenosis after catheter ablation of atrial fibrillation. Circulation. 1998; 98:1769-1775.

Gibson DN et al. Stiff left atrial syndrome after catheter ablation for atrial fibrillation: Clinical characterization, prevalence and predictors. Heart Rhythm, vol. 8, No. 9, 2011.

Tsao HM et al. J Cardiovasc Electrophysiol 2010; 21: 270-277.

Buber J. et al. J Am Coll Cardiol, 2011; 58:1614-1621.

S. Sherrit, G. Yang, H.D. Wiederick and B.K. Mukherjee, Temperature Dependence of the Dielectric, Elastic, Piezoelectric Material Constants of Lead Zirconate Titanate Ceramics, http://mastersonics.com/documents/mmm_basics/general_info/ultrasonics_faq/ferro29.pdf, 1999.

Hansoo Kim and Wolfgang Sigmund. Zinc oxide nanowires on carbon nanotubes. Appl. Phys. Lett. 81, 2085 (2002).

Kern TA. Engineering Haptic Devices. (Ed.) 2009, XXXI, 472 p. 243-276.

Tanaka, Y.; Doumoto, K.; Sano, A.; Fujimoto, H.;, "Development of a sensor system with syringe based on tactile sensing using balloon expansion," Robotics and Automation (ICRA), 2010 IEEE International Conference on, vol., no., pp. 4861-4866, May 3-7, 2010.

Tabata, T. et al. J Am Coll Cardiol, 2003; 41:1243-1250.

Friedman, PA. Heart Rhythm 2012; 9: 1046; "Hitting a Moving Target".

2012 HRS/EHRA/ECAS Expert Consensus Statement on Catheter and Surgical Ablation of Atrial Fibrillation published in Heart Rhythm, vol. 9, No. 4, Apr. 2012, 632-696, Europace Advance Access published Mar. 1, 2012.

Robocast, Robot and sensors integration for Computer Assisted Surgery and Therapy, Dec. 31, 2010.

Indian Pacing Electrophysiol. J. 2012; 12(2): 39-53.

Andrade JG et al. Heart Rhythm 2011; 8(9): 1444-1451.

United States Army Research Laboratory: A Review and Meta Analysis of Vibrotactile and Visual Information Displays, Elliott et al, ARL-TR-4955, Sep. 2009.

Chun KR et al. J Cardiovasc Electrophysiol. 2009; 20(11)1203-1210.

Sarabanda AV et al. JACC 2005;46(10):1902-1912.

Chiba S et al. Electroactive Polymer "Artificial Muscle" Operable in Ultra-High Hydrostatic Pressure Environment. IEEE Sensors Jounral, vol. 11, No. 1, Jan. 2011, p. 3.

Wu J et al. Proc. IMechE vol. 220 Part D: Automobile Engineering. p. 313, 2006.

KurzweilAI, Accelerating Intelligence.news, Tactile technology guaranteed to send shivers down your spine, Aug. 9, 2011.

Leitmann G. Applied Mathematics and Computation 1995 70: 247-259.

Han Y et al. Smart Mater. Struct 20 (2011) 075019, Abstract.

Kesner, S.B.; Howe, R.D.;, "Discriminating tissue stiffness with a haptic catheter: Feeling the inside of the beating heart," World Haptics Conference (WHC), 2011 IEEE, pp. 13-18, Jun. 21-24, 2011.

"Growth and replication of ordered ZnO nanowire arrays on general flexible substrates" Su Zhang, Yue Shen, Hao Fang, Sheng Xu, Jinhui Song and Zhong Lin Wang, J. Mater. Chem., J. Mater. Chem., Sep. 2010.

"Cellular Level Biocompatibility and Biosafety of ZnO Nanowires" Zhou Li, Rusen Yang,Min Yu, Fan Bai, Cheng Li and Zhong Lin Wang, J. Phys. Chem. C, 112 (2009) 20114-20117.

"Piezoelectric-Potential-Controlled Polarity-Reversible Schottky Diodes and Switches of ZnO Wires",Jun Zhou, Peng Fei,Yudong Gu, Wenjie Mai, Yifan Gao, Rusen Yang, Gang Bao, and Z.L. Wang, Nano Letters.,2008.(8),11. 3973-3977.

"Elastic Properties and Buckling of Silicon Nanowires",Cheng-Lun Hsin, Wenjie Mai, Yudong Gu, Yifan Gao, Chi-Te Huang, Yuzi Liu, Lih-Juann Chen,and Z.L. Wang, Advanced Materials.,2008 (20) 20, 3919-3923.

"Flexible Piezotronic Strain Sensor", J. Zhou, Y.D. Gu, P. Fei, W.J. Mai, Y.F. Gao, R.S.Yang, G. Bao and Z.L. Wang Nano Letters, 2008, 8(9),3035-3040.

"Mechanical-Electrical Triggers and Sensors Using Piezoelectric Micowires/Nanowires", J. Zhou, P. Fei, Y.F. Gao,Y.D. Gu, J. Liu, G. Bao and Z.L. Wang Nano Letters, 2008, 8(9), 2725-2730.

"Fabrication of ZnO Nanowire Devices via Selective Electrodeposition",Min Zhang, Zhaoying Zhou,Xing Yang, Xiongying Ye, and Zhong Lin Wang. Electrochemical and Soild-State Letters,11(9) D69-D71 (2008).

Electrostatic Potential in a Bent Piezoelectric Nanowire. The Fundamental Theory of Nanogenerator and Nanopiezotronics,Y.F. Gao and Z.L. Wang Nano Lett., 7 (2007) 2499-2505.

The new field of nanopiezotronics, Z.L. Wang, Materials Today, 10 (2007) 20-28.

Nanowire Piezoelectric Nanogenerators on Plastic Substrates as Flexible Power Sources for Nanodevices, P.G. Gao, J.H. Song, J. Liu and Z.L. Wang Adv. Mater., 19 (2007) 67-72.

Piezoelectric Nanogenerators Based on Zinc Oxide Nanowire Arrays, Z.L. Wang and J.H. Song Science, Apr. 14, 2006: 242-246.

"Pattern and Feature Designed Growth of ZnO Nanowire Arrays for Vertical Devices", J. H. He, J. H. Hsu, C. H. Wang, H. N. Lin, L. J. Chen and Z. L. Wang, J. Phys. Chem. B, 110 (2006) 50-5.

Heart Rhythm, vol. 9, No. 1, Jan. 2012 p. 18-23.

Kim MH et al. Circ Cardiovasc Qual Outcomes 2011; DOI:10.1161/CIRCOUTCOMES.110.951865; AHA.

NEJM 2002; 347: 1825-1833.

Dagres N. et al. J Cardiovasc Electrophys Sep. 2009; 20(9): 1014-1019.

Dong, J et al, J Cardiovasc Electrophysiol, vol. 16, pp. 845-852, Aug. 2005.

J Am Coll Cardiol, 2006; 47:2498-2503, doi:10.1016/j.jacc.2006.02.050.

Vibrotactile Rendering for a Traveling Vibrotactile Wave Based on a Haptic Processor. Sang-Youn Kin and Jeong Cheol Kim. IEEE Transactions on Haptics, vol. 5, No. 1, Jan.-Mar. 2012.

Smooth Vibrotactile Flow Generation using two Piezoelectric Actuators. Kang J. et al. IEEE Transactions on Haptics, vol. 5, No. 1, Jan.-Mar. 2012, pp. 21-32.

Andreu, D, Displacement of the target ablation site and ventricles during premature ventricular contractions: Relevance for radiofrequency catheter ablation, Heart Rhythm, vol. 9, Issue 7, p. 1050, Jul. 2012.

(56) References Cited

OTHER PUBLICATIONS

Kesner, S.B.; Howe, R.D.;, "Discriminating tissue stiffness with a haptic catheter: Feeling the inside of the beating heart," World Haptics Conference (WHC), 2011 IEEE Abstract, Jun. 29, 2011.
Yuen, S. et al, Robotic Tissue Tracking for Beating Heart Mitral Valve Surgery, Medical Image Analysis, p. 1-11, Jun. 14, 2010.
Yuen, S. et al, Force Tracking with Feed-Forward Motion Estimation for Beating Heart Surgery, IEEE Transactions on Robotics, vol. 26, No. 5, Oct. 2010, p. 888-896.
Yuen, S. et al, Robotic Motion Compensation for Beating Heart Intracardiac Surgery, The International Journal of Robotics Research, p. 2-18, 2009.
Kesner, Samuel et al, Design of a Motion Compensated Tissue Resection Catheter for Beating Heart Cardiac Surgery, Proceeding of the 2011 Design of Medical Devices Conference, DMD2011-5271, Apr. 12-14, 2011 Minneapolis, MN USA, p. 1-6.
Kesner, S. et al., Position Control of Motion Compensation Cardiac Catheters, p. 1-10, Oct. 28, 2010.
Zorcolo, A. et al, Catheter Insertion Simulation with Combined Visual and Haptic Feedback, 1999.
Haruta, M et al., Development of Remote-Type Haptic Catheter Sensor System using Piezoelectric Transducer, Extended Summary, p. 5, 2007.
Bethea, B. et al., Application of Haptic Feedback to Robotic Surgery, J Laparoendosc Adv Surg Tech A. Jun. 2004; 14(3): 191-195.
Ouellette, Jennifer, Smart Fluids Move into the Marketplace, The Industrial Physicist, Dec. 2003/Jan. 2004, p. 14-17.
Patel, Nikunj Manubhai, Design of Haptic Force Feedback for Catheter Insertion Mechanism, Dec. 2006.
Pare, Michel; Joseph E. Mazurkiewicz, Allan M. Smith, and Frank L. Rice (Sep. 15, 2001). "The Meissner Corpuscle Revised: A Multiafferented Mechanoreceptor with Nociceptor Immunochemical Properties". The Journal of Neuroscience, Sep. 15, 2001, 21(18): 7836-7246.
Kumar, Saurabh et al., Effect of respiration on catheter-tissue contact force during ablation of atrial arrhythmias, Heart Rhythm 2012; 9: 1041-1047.
Howe, E., The Plymouth Student Scientist, 2009, 2, (1), 90-107.
Savazzi, S. et al., Interhemispheric transfer following callosotomy in humans: Role of the superior colliculus, Neuropsychologia 45 (2007) 2417-2427.
Zhu R, Zhou Z. A Small Low Cost Hybrid Orientation System and Its Error Analysis, IEEE Sensors Journal, vol. 9, No. 3, Mar. 2009.
Han J, Shannon MA. Smooth Contact Capacitive Pressure Sensors in Touch and Peeling-Mode Operation. IEE Sensors Journal, vol. 9, No. 3, Mar. 2009.
U.S. Appl. No. 60/647,102, filed Jan. 1, 2005.
U.S. Appl. No. 60/660,101, filed Mar. 9, 2005.
U.S. Appl. No. 11/584,465, filed Oct. 20, 2006, Abandoned.
U.S. Appl. No. 11/746,752, filed May 1, 2007, Abandoned.
U.S. Appl. No. 11/771,233, filed Jun. 29, 2007, Abandoned.
U.S. Appl. No. 11/848,346, filed Aug. 31, 2007, Abandoned.
U.S. Appl. No. 60/855,820, filed Nov. 1, 2006.
U.S. Appl. No. 61/270,924, filed Jul. 15, 2009.
U.S. Appl. No. 61/396,575, filed May 29, 2010.
U.S. Appl. No. 61/341,129, filed Mar. 27, 2010.

\* cited by examiner

MINIMALLY INVASIVE CARDIOVASCULAR SUPPORT SYSTEM WITH TRUE HAPTIC COUPLING

RELATED APPLICATION

The present application claims the benefit of U.S. Provisional Application No. 61/517,073 filed 13 Apr. 2011, which is incorporated herein in its entirety by reference.

FIELD OF THE INVENTION

This disclosure relates to a family of hand-held minimally-invasive surgical (MIS) cardiac resuscitation components and field-kits with tactile force feedback that acquires anatomic and mechanical data that is tactually represented to an operator via a haptic interface to facilitate cardiac resuscitation.

BACKGROUND OF THE INVENTION

Currently available techniques and technology for providing cardiac mechanical support to a patient with heart problems and in need of cardiac resuscitation are either non-invasive and entirely external in the form of cardiopulmonary resuscitation (CPR), or highly invasive and surgical, typically in the form of an open heart gross thoracotomy (a so-called "cracked-chest" surgery).

While CPR is a well-recognized and highly effective technique for short-term emergency situations to bridge a patient back to cardiac resuscitation by the restoration of a normal sinus rhythm, it is not a technique that can be consistently and effectively used for longer periods of time or in situations involving physical damage to the patient's heart.

Most current surgical and invasive techniques and technology for cardiac resuscitation require a gross thoracotomy (usually in the form of a median sternotomy) to gain access into the patient's thoracic cavity. A surgical saw or other cutting instrument is used to dissect the sternum longitudinally, allowing two opposing halves of the anterior or ventral portion of the rib cage to be spread apart (thus, the "cracked-chest" nomenclature). A large opening into the thoracic cavity is thus created, through which the surgical team may directly visualize and operate upon the heart and other thoracic contents. Not surprisingly, a gross thoracotomy procedure involves substantial mortality risks (i.e., risk of severe immediate and eventual surgical complications, including death).

Once the gross thoracotomy is completed, a medical professional can utilize direct manual heart massage where the heart is grasped and periodically squeezes the heart in an attempt to restore blood flow. For longer term cardiac resuscitation, a left ventricular assist device (LVAD) therapy can be utilized wherein the LVAD (essentially a continuous, non-pulsatile, and externally-powered mechanical pump somewhat akin to an artificial heart) is positioned in an intracardiac location and attached in fluid communication with the heart. An LVAD typically requires an external battery pack or external vacuum port to power the LVAD for prolonged periods of time as a bridge toward ultimate cardiac transplantation.

Another less invasive surgical approach to cardiac mechanical support uses an intra-aortic balloon pump (IABP) that is inserted through the femoral artery into the descending aorta of a patient. An IABP functions to reduce afterload and improve cardiac output on a temporary basis; however, the use of an intravascular approach always increases the possibility of clots and strokes due to the presence of a mechanical device within the patient's vascular system.

Accordingly, there is a need for better solutions for providing acute cardiac resuscitation and cardiovascular mechanical support including support for select intrathoracic organs to a wide variety of patients. Such patients range from those who have incurred post-operative complications (e.g., following heart surgery) to those who have suffered traumatic injury to the thorax. Viable solution(s) that can address the shortcomings of the current techniques and technologies for providing cardiac mechanical support to patients in need of same presents an opportunity to advance the standard of care.

SUMMARY OF THE INVENTION

The current disclosure provides a family of MIS instruments, components, and systems for exploring, supporting and treating the heart and surrounding structures via MIS techniques (i.e., without performing a gross thoracotomy) that is augmented with one or more haptic interfaces. The technologies, techniques, and field-kits described herein have broad clinical applications ranging from the treatment of patients who have incurred post-operative complications (e.g., following heart surgery) to patients who have suffered traumatic injury to the thorax to patients with a need for alternate surgical approaches for treating cardiothoracic conditions secondary to anatomical anomalies (e.g., congenital heart disease).

Ordinarily, the characteristics of surgical equipment and bodily tissues prohibit an operator from sensing tissue and organ characteristics as they are generally secondary to signal noise and attenuation and dampening effects. This disclosure describes a family of systems that provide true, rather than virtual coupling between an inserted cardiac instrument and operator by eliminating the attenuation and dampening effects of the intervening tissues and surgical tools. Sensors located at the distal portions of the resuscitation system acquire data that is processed and used to generate a three dimensional tactile recreation of the intra-thoracic and cardiac environment. The device provides electromechanical support while gathering real time physiologic information. Via a haptic interface, the operator experiences a "real feel" of the cardiac, extra-cardiac and intra-thoracic anatomy through a haptic heart model, instrumented haptic glove or other multi-fingered haptic interface and can utilize this haptic information to appropriately position and engage the support system to effect cardiac resuscitation and cardiovascular mechanical support of the patient.

In various embodiments, the support system can function manually, semi-automatically and run autonomously providing patients with impaired cardio-respiratory function with continuous support. Discrete embodiments herein can serve as a cardiac assist mechanism that enhances and promotes CO for patients suffering from congestive heart failure, cardiovascular collapse, traumatic injury, cardiogenic shock, electro-mechanical dissociation (also known as pulseless electrical activity or PEA), and post-open heart surgical low CO states such as those encountered following a thoracotomy procedures (whether performed on an as-scheduled basis in the sterile environment of an operating room or acutely and immediately in a open-field setting), to name just a few. Several exemplary embodiments are configured as minimally invasive operative tools that can treat diseases of the pericardium including constrictive pericarditis, pericardial effusion and pericardial tamponade, to name just a few pathologic cardiac states. Additionally, the teaching herein enables sensing cardiac activity (e.g., intrinsic and evoked) and generating electrical impulses for cardiac pacing, defibrillation, and electromechanical resynchronization.

In contrast to the prior art, the instant disclosure describes, depicts, enables, and claims certain multi-fingered end-effectors optionally coupled to a variety of instrumented haptic interfaces for various applications that provide multipoint contact between a user and a real environment. The current disclosure involves a family of multifunctional end-effector elements that can be individually configured as a multi-fingered array of expandable and collapsible members (e.g., surgical blades, elongate resilient foldable arrays, semispherical webbed components, and various and diverse sensors coupled thereto) that can be deployed into contact with a target volume of tissue, the vasculature, or various organ(s) of a subject using minimally invasive surgical, or MIS, techniques. In an exemplary application, one or more of the members can be positioned along or through extra-cardiac tissue planes and/or at intra-cardiac regions if needed. The members can be customized to the actual physiology of a subject and have multiple applications including the delivery of closed chest cardiac massage for subjects of all sizes, ages, heart dimension and size, and heart failure status, for example. During insertion a physician-operator is provided with tactile feedback that guides positioning of the cardiac support device, in one form, and helps the physician program optimal settings for delivering mechanical and/or electrical support given the physiologic state and condition of a given subject.

Haptic rendering is conventionally understood to provide a master (the operator) with a virtual experience that simulates a real environment. At least one distinguishing feature or aspect of the present disclosure is that specialized and unique haptic rendering is utilized to provide the physician-operator with a real experience (herein, newly defined as "true coupling" providing essentially direct tactile perception of the interaction, state and location of a working end-effector) which is a haptic representation of actual real time, anatomic and physical events rather than a simulation.

Certain terms used in this disclosure are intended to convey at least a slightly different meaning than might be otherwise understood; for example, "appreciate" and "appreciation" should be construed to cover all synonyms for "feel" or "perceived." The terms or phrases, tactile, tactual, and haptic are likewise intended to relate to qualities of an instrumented tool or appliance in contact with or capable of being perceived by an operator (e.g., digits/hands, toes/feet, arm/leg, head/face, etc.). These qualities convey that a working end of the tool or appliance has encountered a surface, a fluid, or an object, for example and relate to discrete characteristic of same. Such qualities can take various forms such as: physical perturbations (e.g., constant or changing vibration(s); a change in size, temperature, or surface features; or a perceived change in a center of gravity; a constant torque or a change in torque); a linear acceleration, a gyroscopically-induced phenomenon, and the like), accompanying or independent auditory perturbations, olfactory and/or taste-related phenomenon and with one or more of the foregoing optionally including visual cues (e.g., discrete icons displayed, changing colors of a tool or appliance or "flag" on a display, change in ambient, artificial light, steady-state to flashing beacons, and the like).

Thus the haptic heart resuscitation systems disclosed herein include including in one form an array of optionally finger-shaped, collapsible and expandable blades that can be inserted into the body and used to dissect and enter specific tissue planes including the extra-cardiac space between the pericardium and the epicardial surfaces as well as specific intra-cardiac locations. By way of example, one or more of the devices described, depicted, and claimed herein can be inserted into the thorax of a subject without performing a sternotomy (e.g., using a small sub-xyphoid incision) and positioned about the heart or an organ for delivery of diverse mechanical and electrical support and therapy.

The present devices provide the physician-operator with tactile feedback anatomically guiding insertion or deployment to a desired position, and once positioned acquires diverse electrical parameters or characteristics; biological/fluid-based parameters or characteristics (e.g., blood chemistry and constituents thereof, such as hematology, electrolytes, liver enzymes, nitrogen elements, proteins, lipids, etc.) which are indicative of the performance or lack thereof of certain organs and biological control systems; oxygen saturation (venous and arterial oxygen content); and mechanical diagnostic parameters and characteristics and diverse related data used or useful to deliver electrical and mechanical support to an organ and/or therapeutic pacing and defibrillation to a heart.

In various embodiments, the devices can be operated manually (e.g., directly by a single physician or jointly with a directly-attending physician or clinician at a patient location and a remotely-attending physician working controlling the end-effector(s)) or can be implemented as an adjunct or an adapted workpiece for a robotically-controlled surgical system.

In the latter case, an exemplary robotic system also controlled directly (i.e., in close proximity to, or in a common operating room with, a patient) or remotely by a physician provides an alternative to open heart surgery is the robotically guided, thoracoscopically-assisted robotic system marketed under the tradename of the da Vinci™ system by Intuitive Surgical, Inc. of Sunnyvale, Calif. Instead of requiring a sternotomy, the da Vinci system uses a minimally invasive approach guided by camera visualization and robotic techniques.

DETAILED DESCRIPTION OF THE DRAWINGS

Figure 1:
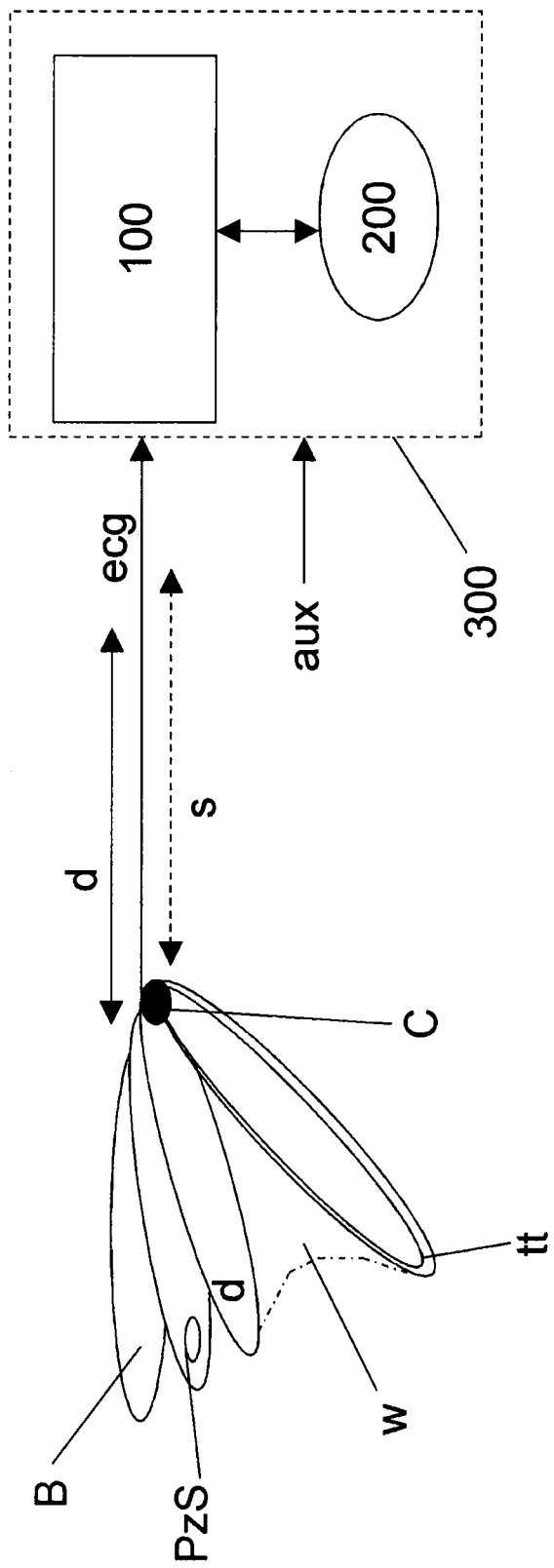
FIG. 1 is shows a diagrammatic representation of an embodiment of the subject matter described and claimed herein.

Referring now to FIG. 1, a system constructed in accordance with this disclosure that includes at least one end-effector working end 102. The working end-effector 102 can include a plurality of finger-like projections (generically termed "end-effectors" or "blades" herein), denoted by the letter "B" and reference numeral 104 from time to time herein, that are fitted with a first set of sensors 106 (and denoted as "PzS" in FIG. 1) for obtaining gross mechanical information, a second set of sensors 108 (denoted as "tt" in FIG. 1), hereinafter called (tactile) sensors for acquiring qualitative data or properties of a nearby surface such as from various biological tissue or organs of a subject (e.g., texture, pulsatile motion, elasticity, and the like), and an intermediate structure such as a supportive and insulating webbing material 110 (denoted as "w" in FIGS. 1 and 2) that can contain a fluid (e.g., biocompatible gas, air or a liquid medium such as saline) as an operative part of a pneumatically- or hydraulically-driven contractile system optionally coupled to a haptic interface 100. The blades 104 (B) are not necessarily similar and can serve multiple discrete or cooperative mechanical functions including being used as a surgical dissection tool, cardiac compression apparatus, electrocautery units, a platform for diverse EGM sensors, pressure sensors, and/or oxygen sensors or low power cardiac pacing and high power defibrillation electrodes. A collection of such blades 104 operate as an end-effector 102. Data is bidirectionally communicated between the end-effector 102 and haptic interface 100, as an electrical or electromagnetic signal over a standard data channel (denoted as "d" in FIG. 1) or via one or more pneumatically- and/or hydraulically-driven communication or control lines or fluid-filled lumens. Monitoring of cardiac electrical activity (e.g., surface echocardiogram, or ECG or an internal electrogram, or EGM) can occur via conventional ECG skin surface electrodes or from conductive material that is part of the blades 104. Sensors 106,108 (e.g., piezoelectric, force, strain gauges, optical) acquire mechanical data that is used to construct part of the final haptic representation (touch and/or force feedback) plus optionally, non-force sensor data that can be combined so that the operator perceives all such sensor data at the haptic interface 100. The acquired data is input into the processor 200 that processes (e.g., provides haptic rendering) the input data converting the information to signals output to the haptic interface 100. Haptic interface 100 can comprise an instrumented haptic glove having actuators coupled to respond to sensor data signals, multi-fingered haptic interface(s) for one or more digits of a user, an exoskeleton type interface providing contact with a users hand, arm, or facial anatomy for example, a non-rigid, deformable virtual heart model that includes auditory, visual, and mechanical cues to a user, or other simulation feedback system or device. A virtual heart model or as referred to herein as "haptic heart" can comprise an oblong shaped compressible device that conveys mechanical properties of a subject's heart that is driven by actuators coupled to sensors and sensor signal processing to provide a realistic sensation to a user (e.g., tissue contractility or elasticity, temperature, pulsatile pressure and fluid flow and the like) similar to a typical mammalian heart.

Suction and irrigation can be provided to an end-effector 102 or one or more blades 104 (or webbing 110) using fluid passageways or conduits, multi-lumen or conventional tubes 112 (denoted as "S" in FIG. 1) and the like formed into the respective structures and coupled to suitable vacuum source(s), fluid pumps and optionally auditory representations of suction, irrigation (i.e., fluid flowing) and the magnitude of same. A control system 300 integrates sensor and other data acquired by an end-effector 102 or a blade 104, a haptic interface 100, a processor 200, and remote or outside surface physiologic data and auxiliary data derived from auxiliary physiologic support equipment, for example. Auxiliary equipment can include but is not limited to echocardiographic imaging technology, radiographic/fluoroscopic equipment, three dimensional localization and/or surgical navigational systems, respiration monitoring, acoustic-ranging-, electromagnetic-, magnetic-, electrical- and/or impedance-based anatomic mapping technologies (e.g., Biosense Webster CARTO and CARTO 3 systems, St. Jude Medical EnSite System or MediGuide Magnetic Technology) collectively depicted in FIG. 1 with reference numeral 400. The control system 300 optimizes the virtual coupling between the end-effector(s) 102 and blades 104 and haptic interface 100 and automatically programs the end-effector(s) 102 to function as a cardiac assist device by providing contractile force—synchronized via diverse cardiac sensor signals—to at least a portion of a ventricle of a subject, for example. Attenuation or impedance based haptic interfaces can be implemented within the processor 200 and control system 300 depending on the sensed data (e.g., force-based, ECG, EGM, acceleration-based, fluid flow-based, CO-based, or ventricular wall velocity-based information at a given moment in the cardiac cycle such as at the end-diastolic or end-systolic portion of a cardiac cycle).

Figure 2:
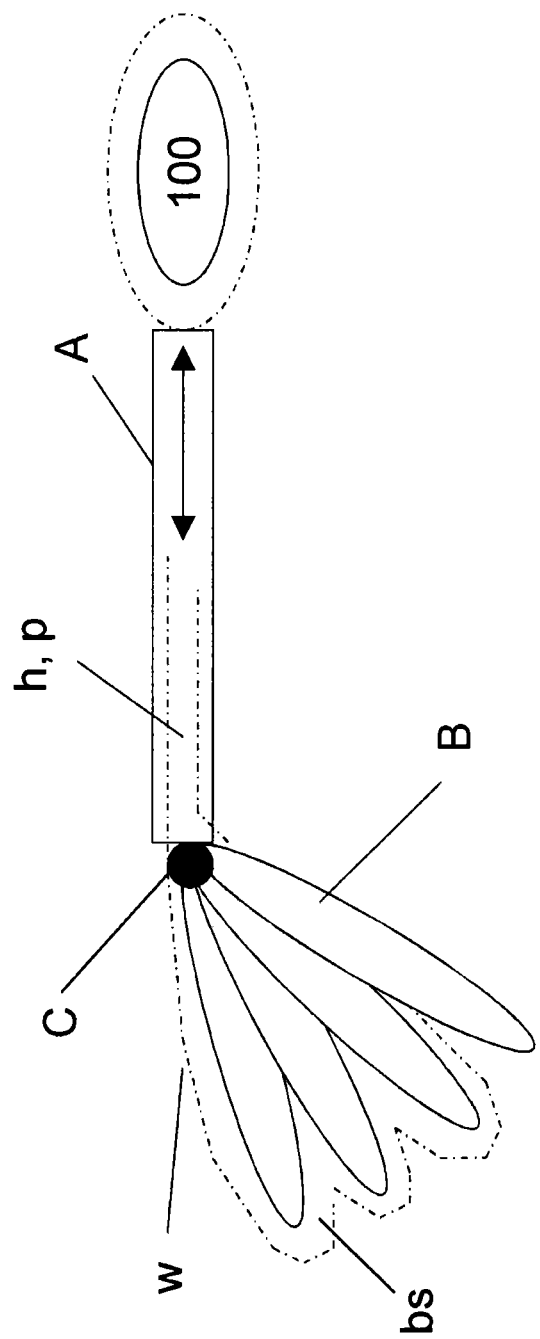
FIG. 2 represents an embodiment of the introduced in FIG. 1.

FIG. 2 depicts how, in one embodiment, one or more of the blades 104 can be surrounded or linked and supported by a viscous liquid or other fluid contained within gaps or between layers of insulating webbing 110. The liquid or other fluid simply transmits the forces applied via remotely-coupled pumps and/or suction or vacuum sources upon the intrathoracic end-effectors 102 (e.g., via a compressible, but resilient fluid filled blade and fluid vessel or conduit coupled thereto) and haptic interface 100 hydraulically, via a hydraulic line, h, or pneumatically, via a pneumatic line 118 (also denoted as "p" in FIG. 2) enabling transfer of gross mechanical energy (e.g., resistance, recoil, low frequency vibration) to be transmitted between the haptic interface 100 and end-effector 102 or discrete blades 104 thereof. This gross mechanical energy supplements the finer detailed data acquired by the end-effector sensors 108 and also enables the operator to generate forces upon the heart for resuscitation purposes (e.g., closed chest cardiac massage) while receiving appropriate sensory information relating to the mechanical properties of the external cardiac surface (e.g., the epicardial surface within the pericardial sac) as well as actual internal mechanics and characteristics of the subject heart (e.g., cardiac dilatation, contraction or heart rate, CO, fluid flow, EGM, electromechanical dysynchrony, pulse-less electrical activity or fine ventricular fibrillation, bradycardia, or tachycardia, etc.).

As the time for mechanical data to be transmitted to the operator via a pneumatic or hydraulic line and electrical data to be received at the haptic interface will differ, a built in time constant or time delay, t, can be added to the electrical data via the processor 200. Thus, a user can opt to remove the physiologic time delay between electrical activity and actual mechanical cardiac events and such combined data is appreciated synchronously as if electrical and mechanical cardiac events and data transmission related thereto occurred simultaneously. Calculation of the time delay or time constant "t" can be made by processor 200 prior to system operation, adjusted from time to time based on actual sensor signals, or arbitrarily adjusted (e.g., using a predetermined time interval such as 10-150 ms). For example, this calibration is accomplished by calculating the time between when an auto-generated impulse from the end-effector 102 is communicated and sensed both mechanically and electrically. However, when only electrical or electromagnetic data is utilized within the system "true" or real haptic coupling will occur without a detectable time delay if robust computational techniques are utilized as discussed below.

More specifically, the end-effector 102 can consist of one or more finger shaped blades 104 (also denoted as "B" in FIG. 1) some having variable degrees of sharpness (blunt to razor-sharp). The blades 104 can be flat, deformable, having lateral dimensions of a few millimeters, and able to be in an overlap (interlocking or "fanned") positioned and adapted to be inserted through a small MIS incision (e.g., 0.25-2.0 cm). If more than one blade 104 is used, the blades 104 are initially overlapped for device storage, during insertion or deployment and at time of withdrawal. Once inside the thorax the blades 104 can be opened to varying angles or spread apart depending on operator preference and in one embodiment, deliver pacing and/or defibrillation therapy via the blades 104 or from electrodes temporarily or permanently delivered within the thorax or upon and within cardiac structures (e.g., coronary sinus, left ventricular myocardial surface, etc). Haptic feedback provides the operator with a means to tactually appreciate that anatomic properties of contacted tissue and even fluid/blood flow in the extracardiac space (e.g., pericardial fluid) and intracardiac (coronary sinus blood flow) locations.

A central pivot or rotary joint 120 (denoted as "C" in FIGS. 1 and 2) is present about which the blades 104 open and close. The central pivot 120 has a fixed component which in one embodiment is a central ring held stationary by a torque rod (not shown) attached to a fixed portion of the proximal, hand held section, handle, or arm 122 (also denoted as "A" in FIG. 2) of the support system. Other types of pivot joints can be used to provide rotation, of course. In one embodiment, the rotating component has a central connecting core which is robotically controlled and responds to the operator's commands through a control line (such robotic control is schematically illustrated in FIG. 1 as functional block 500). The external controller can be under manual control of the operator or run autonomously by a computer/processor 200 and control system 300 that drives the system as described in more detail below.

In an embodiment, the angles between one or more of the blades 104 are controlled by the operator spreading his or her fingers apart to the desired amount (e.g., upon a haptic interface 100 such as within an instrumented, haptic glove or via a multi-fingered haptic interface or the like). Each blade 104 can have a different structure and can be adapted to perform different functions. One or more of the blades 104 is fitted with one or more flexible hinge joints (124/H1 and 126/H2 in FIG. 3) that enable the end-effector to grasp (blade flexion and extension) and oppose anatomic structures or even grasp, position and deliver a permanently implantable device (e.g., a medical electrical lead including pacing electrodes) into an intrathoracic, extra-cardiac or intra-cardiac location (e.g. pacing/sensing electrode configuration as opposed to myocardium, subcutaneous defibrillator electrodes). Kinesthetic and proprioceptive feedback capabilities are provided with position sensors 106' located at each hinge joint 124,126 and within the haptic interface 100 (e.g., instrumented haptic surface or glove). The design of the fingers of the blade members 104 can be simplified and contain simple hinge joints for flexion and extension or be more complex simulating a fully dexterous robotic hand and arm construct. Microfabrication techniques can be used and applied as to sufficiently miniaturize the needed components for MIS applications and procedures.

Figure 3:
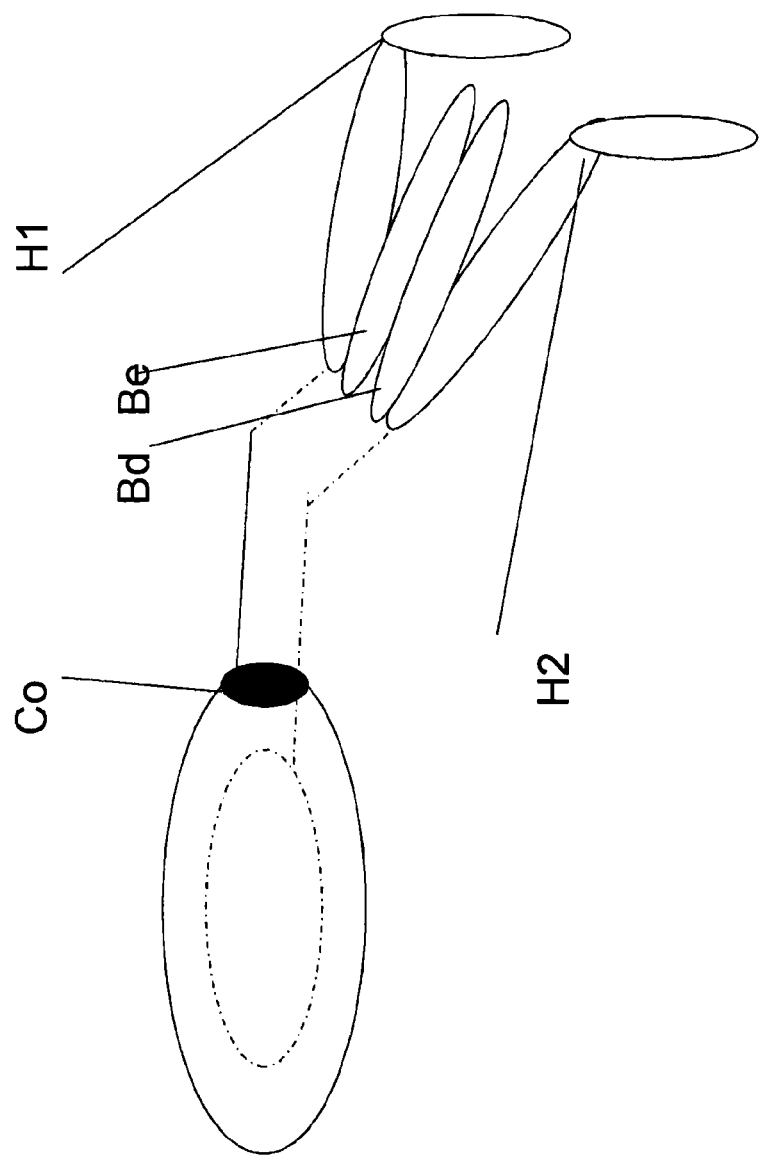
FIG. 3 depicts haptic interfaces, a so-called haptic heart and glove model, and blades and a connector for coupling information to and from a haptic glove and a haptic heart model.

Referring to FIG. 3, hinge joints 124,126 (also denoted as H1 and H2), present on the two most peripherally located fingers or blades 104 of an end-effector 102. The two internally located blade fingers can be used for dissection 128 (denoted as "Bd" in FIG. 3), and electrocautery 130 (denoted as "Be" in FIG. 3). Torque-angle data of each hinge joint 124,126 is determined by a kinesthetic sensor such as a force/torque transducer at the hinges. A similar transducer is present at the haptic interface within a haptic glove or alternate multi-fingered haptic interface. The proximal (haptic interface) and distal (end-effector) torque angle data are transmitted to the controller and adjustments made as to optimize coupling of actual resistance and the user's perceived stiffness to flexion and extension. Other means of optimizing coupling of the action and perceived mechanics between the end-effector 102 and operator's haptic interface 100 are within the scope of the instant disclosure.

An arm 122/A, disposed between the end-effector 102 or blades 104 thereof and haptic interface 100 enables the operator to generate torque on end-effector 102 of the system and palpate torque from cardiac twisting motion (FIG. 2). The torque force is sensed by a sensor at the connection between the central pivot joint, C, as seen in FIGS. 1 and 2, and torque arm A (FIG. 2), and is presented to the operator at the haptic interface 100 and generated manually by the operator's action on the torque arm A upon the end-effector 102 and vice versa.

The blades 104 and attached sensors 106 (PzS in FIG. 1) are connected via torque arm 122 A and data channel to the processor 200 and control system 300 that is situated outside the body of a subject. The end-effector 102 and arm 122/data channel structure "d" are able to be sterilized and used for repeated applications. The processor 200 and control system function along with a haptic glove or other haptic interface 100 which can be in form of a compressible, "real feel" model of the heart (the haptic heart) for system operation. The inserted blades interact and communicate bidirectionally via data channel D (e.g., analog or digital electric or electromagnetic signals) with the processor 200, control system 300 and haptic interface 100, and in one embodiment, via one or more of pneumatic, hydraulic lines or pipes. Electrocardiographic monitoring, or ECG monitoring, is provided to the control system either from separate electrodes or recordings acquired from the inserted blade(s) via channel ECG.

Each thin (millimeter scale) malleable blade is preferably constructed of conductive metal alloy (which can be a memory shape alloy such as copper-aluminum-nickel) which are coated with varying degrees of insulation. The edges of one or more lower profile blades 104 are able to be exposed for purposes of cutting by being separated from neighboring non-cutting blades 104. Specific blades 104 are used for receiving electrical information and delivering electrical impulses (e.g., sensing, pacing, defibrillation and the like), electrocautery or fixating electrodes. The insulation can be composed of any insulator including DACRON material. By way of example, and in one embodiment, at least some of the blades 104 are covered with a sleeve that is made of electrically insulating materials such as silicon or polyurethane (FIG. 2 peripherally located blades 104). In one embodiment, certain portions of the sleeve are conductive for the sensing and delivery of electrical stimulation for sensing cardiac electrical activity, pacing and defibrillation. Alternatively, the sleeve covers only a portion of the blade 104 and the exposed blade itself serves as a conductor/electrode. In another embodiment, the blades are composed of energy harvesting material or alloy as is described in more detail below.

In another preferred embodiment, the insulation also serves as an elastic web 110 (denoted as "w" in FIG. 1) between each blade 104 of an array of several individual blades and enables the blades 104 and insulation or webbing 110 to conform to the natural shape of the heart. Material suitable for such an application includes foamed Neoprene or polychloroprene. In such an embodiment, the properties of the blades 104 (e.g., memory shape NiTi alloy or the like) and optionally insulating webbing 110 are such that they become more malleable at body temperature and have greater stiffness prior to and during insertion and initial tissue dissection. The elasticity of the webbing 110 at body temperature is optimally within the range of normal and pathologic cardiac tissue (e.g., 1.5-4 kPa). The webbing 110 is in a folded up position prior to blade separation or expansion. Preferably, microfabrication techniques are used to construct a web structure that is low profile in both the folded and open position.

The conductive portion on the sleeve or of the blade(s) 104 can have a large surface area or be separated into multiple conductors which are separated by insulation, to define unipolar, bipolar and multipolar electrode configurations. Each blade 104 can serve as a pole to complete an electrical circuit and have a common ground or reference potential that is positioned intra-thoracic or externally located such as a transcutaneous grounding pad.

In one embodiment, delivery mechanisms for permanently fixating electrodes are incorporated into the blades 104 as known by those experienced in the art (e.g., screw fixation mechanisms for epicardial leads). Alternate methods for placing and fixating electrodes are within the scope of the instant disclosure, such as a fishing hook-shaped mechanism that deploys during separation of the inserted blades 104 (denoted by an arrow in FIG. 6), effectively hooking or pinching onto the tissue for fixation purposes (see insert FIG. 6). The electrodes can be composed of mechanical transducer or sensor type configurations of a discrete material such as piezoelectric material.

Sensors, or tactual tips 106 (denoted as "tt" in FIG. 1), along the perimeter of the blades 104, serve to acquire subtle tactual information that is transmitted to the operator, in an embodiment, via a haptic glove or multi-fingered haptic interface 100. The tactile tips 106 are electrically isolated from the electrodes or conductive portions of a blade 104. The tactual tips 106 can be composed of any sensor capable of acquiring mechanical information (e.g., piezoelectric sensors, force sensors, optical sensors, deformation-based tissue softness sensor). This transmitted data can be conveyed using mechanical means (e.g., pneumatic, hydraulic), optically, and/or via electrically transmitted signals (e.g., current, voltage, impedance, electromagnetic) in analog and/or digital format to the control system 300 and haptic interface 100.

The tactual tips 106 provide the necessary anatomic and mechanical data to the operator reproducing gross anatomic features (e.g., vasculature, myocardium, fibrotic tissue) and fine structural details such as tissue texture, roughness, softness, elasticity that relate to normal and pathologic tissue biomechanical characteristics (e.g., due to compromised or infarcted myocardium). Specific sensor designs capable of acquiring the needed data are utilized and suitable haptic rendering techniques are applied to optimize true haptic coupling.

Piezoactuators, vibrotactile actuators, electromagnetic vibration motors or alternate simulation mechanisms located within the haptic interface (e.g. fingertips of the haptic glove(s)) provide non-virtual, true coupling between the end-effector 102 and haptic interface 100. In order for true coupling (rather than virtual coupling) between the anatomic structures at the level of the end-effector and augmented reality haptic interface (e.g. haptic heart or glove) to occur, system processing and haptic rendering within 200 ensures that both time dependant and space dependant components are considered in the final haptic representation.

Interface modalities that exploit natural human fingertip capabilities are used to create a "haptic surface." For example, piezoelectric actuation techniques enable reproduction of compressible and tensile strains at different areas of the fingertips. Surface features such as texture, roughness, friction, smoothness, bumpiness, edge detection and the like can be reproduced at the haptic interface 100 using a variety of devices. The system is capable of detection of the direction of shear force that displaces, deforms and stretches the end-effector's sensors (e.g. on the cardiac surface) and communication of such physiologic and mechanical properties to the operator's skin at the haptic interface. This can be accomplished, for example, using tangential skin displacement via miniature shear displays incorporated into the haptic interface (e.g. distal portions of a haptic glove).

The acquired analog data (e.g., by piezoelectric sensors) can be left in an analog format and be transmitted as data using a specific electronic signature (voltage or current amplitude as a function of time) presented at the haptic interface as an analog signal without haptic rendering and without analog to digital conversion. In this embodiment, conversion of electrical data as force and velocity information at 100 is accomplished using comparable sensors (e.g., piezoelectric transducers/actuators) at both the level of the end-effector and operator interface. Signal amplification can be controlled with an amplifier as known. Such analog to analog data transmission provides the purest, most true haptic coupling with full system transparency. Such a mirror image representation of actual events will be useful for the display of more gross anatomic and physical characteristics (e.g., respiration, cardiac contraction) rather than more subtle tissue properties.

Haptic rendering that require data digitization and complex processing facilitates the operator's ability to appreciate fine detailed information about cardiac structure and function. Processing of large amounts of data in real time requires robust computing techniques. Hyperelastic nonlinear models have been used to achieve realistic soft-tissue simulations. Advances in parallel computing techniques such as the concurrent utilization of fixed point computing units on a field-programmable gate array (FPGA) device along with suitable computer-readable memory and the like have enabled real-time simulation of three dimensional linear elastic deformation models at high frequency update rates. The application of developing techniques such as quantum computing adds virtually imperceptible processing delays due to computation. The implementation of recent advances in computational algorithms will be especially important for reproduction of the tactile properties of a non-rigid deformable object that is in constant motion.

Use of purely digital information (rather than data that remains as an analog signal or requires A/D and D/A conversion) at both the end-effector and for data transmission to the haptic interface is within the scope of the instant disclosure. By way of example, force sensing at the end-effector can be accomplished by using tri-axial fiber optic sensors (U.S. patent application publication number 20080009759 the contents of which are hereby incorporated by reference herein). Electromagnetic signal coherence is affected by applied force and can be used to quantify three-dimensional force upon sensors located within the thorax and opposed to cardiac tissue. As noted herein above, data transmission in this application can occur electromagnetically with fiber optic signals, for example to decrease possible interference between certain ionizing radiation visualization systems or magnetic resonance imaging systems and derivatives thereof.

The following non-patent references describing different options for implanting parts or aspects of a haptic interface are hereby incorporated herein in their respective entities:

Proctor R W et al. Implications of Compatibility and Cuing Effects for Multimodal Interfaces. Proc. Int'l Conf. Human-Computer Interaction, vol. 11, 2005 and Easton R D et. al. Transfer between Vision and Haptics: Memory for 2D Patterns and 3D Objects. Psychonomic Bull. And Rev., vol. 4, pp. 322-325, 1997;

Frisoli A. et al. Kinematic Design of a Two Contact Points Haptic Interface for the Thumb and Index Fingers of the Hand. ASME J Mechanical Design, vol. 129, pp 520-529, 2007;

Mafi R, et. al. A parallel Computing Platform for Real-Time Haptic Interaction with Deformable Bodies. IEEE Transactions on Haptics 2010, Vol. 3, No. 3. p 211-223; and Gleeson B T et al. Perception of Direction for Applied Tangential Skin Displacement: Effects of Speed, Displacement, and Repetition. IEEE Transactions on Haptics 2010, Vol. 3, No. 3 pp 177-188; and Chubb E C et al. ShiverPaD: A Glass Haptic Surface That Produces Shear Force on a Bare Finger. IEEE Transactions on Haptics 2010, Vol. 3, No. 3, pp 189-198.

Both active and passive exploration aspects of data acquisition are incorporated within the haptic display, optimizing the final user's tactile sensitivity. In other words, the motion of the cardiac structures and anatomic landmarks affect the acquired sensor data and haptic representation (passive) and the active exploration of the user's fingers or hand and the like within the haptic interface (e.g., an instrumented haptic glove) directs the motion of the inserted sensors thus having a combined affect (passive and active) on the information coded within the processor 200. Input from the haptic glove(s) into the processor 200 which directs the action of the inserted end-effector 102 (finger-like blades 104) is provided with a variety of mechanisms not limited to inertial motion sensors, accelerometers, gyroscopes, piezoactuators, magnetometers or other means as understood by those experienced in the art.

Thus, the operator's motion is reproduced at the level of the end-effector BS and changes in finger separation joint position etc. within the haptic interface (e.g., an instrumented glove or the like for one or more digits of an operator) result in a similar action (e.g., pitch, yaw, roll) accurately controlling the spatial configurations and the respective angles and relative positions of the blades 104. In an embodiment, three-dimensional spatial localization in real time is determined at least in part with external diagnostic equipment that identifies the location and position of various aspects of the end-effector and operator's hand(s). By way of example, a three dimensional navigational system that uses impedance information between surface electrodes and the tactual tips and hinge joints is used to provide position information (e.g., electroanatomic mapping and/or localization). This is input into the auxiliary port depicted in FIG. 1. Other types of navigation systems as known by those experienced in the art can be utilized (e.g., magnetic, radiographic).

Suction and irrigation can be provided via one or more functional small canulae, S, that operatively couple to one or more of the inserted blade members 104. MEMS technology and nanotechnology based fabrication techniques can be utilized to develop a sophisticated cardiac support device that is microfabricated including manufacturing of webbing materials, conductors, blades, suction cannula and the like. In one embodiment, ultrasonic and/or thoracoscopic imaging technology (e.g., charge-coupled device, ultrasound, fiber optic imaging etc.) is incorporated into the inserted instrument along the perimeter of one or more of the blades 104 as to enable the operator to visualize device placement and the cardiac anatomy. Introduction of the blades and associated hardware can be done in various locations including sub-xyphoid, parasternal, intercostal. More rigid blades as well as hollowed sheaths can be implemented to access specific sites where dense connective tissue (e.g. via an intercostal approach) may impede delivery of the necessary hardware and for connecting various components of either temporarily or permanently implanted systems. Leads or wiring can be left in place, tunneled and connected to permanently implanted devices used for pacing and/or defibrillation and monitoring. Haptic feedback assists in the positioning of such hardware.

System Operation

The following is a case example of how a haptic heart and instrumented haptic glove, or haptic interface, can function as a device for cardiac mechanical and electrical resuscitation and for continuous cardiovascular support (including support for select intrathoracic organs) in a patient suffering from multiple complications (e.g., following open heart surgery). The system is in no way limited to functioning in the described manner and can be utilized in any number of ways.

A patient undergoes open heart surgery (or other cardiovascular procedure such as coronary stenting, ablation of cardiac arrhythmia or implantation of a cardiac rhythm management device (e.g., single-, double-, or triple-chamber pacemaker, defibrillator, LVAD)). The patient has a weakened heart muscle or cardiomyopathy and develops what is termed a low CO state resulting in poor organ perfusion, low blood pressure, reduced or low heart rate and the like. Since the blood pressure is low and the patient is essentially entering into cardiogenic shock, the patient is generally not responsive to intravenous medications. Such an occurrence is unfortunately relatively common, especially after open heart surgeries.

A cardiac ultrasound is oftentimes performed and readily identifies blood accumulating within the pericardial sac, a pericardial effusion, with impending cardiac tamponade that results when the blood compresses the heart until it ceases to function.

Figure 4:
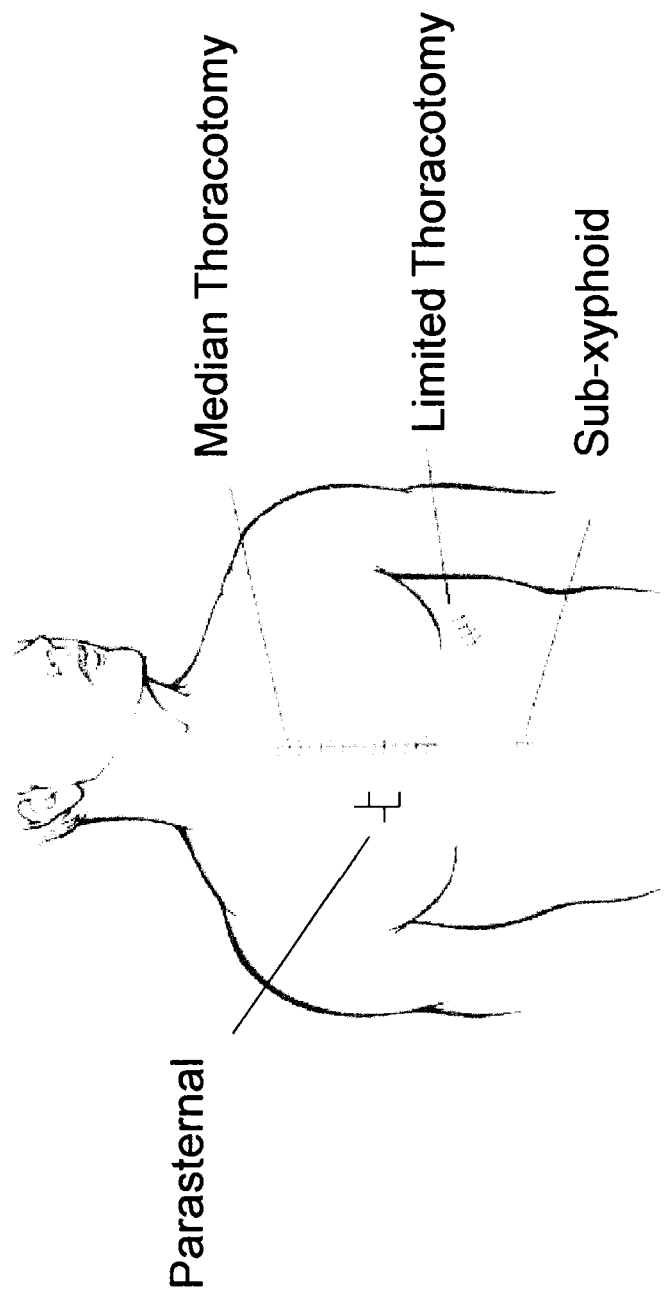
FIG. 4 depicts a prior art version of possible thoracic entry locations for a device according to the disclosure.
Figure 5:
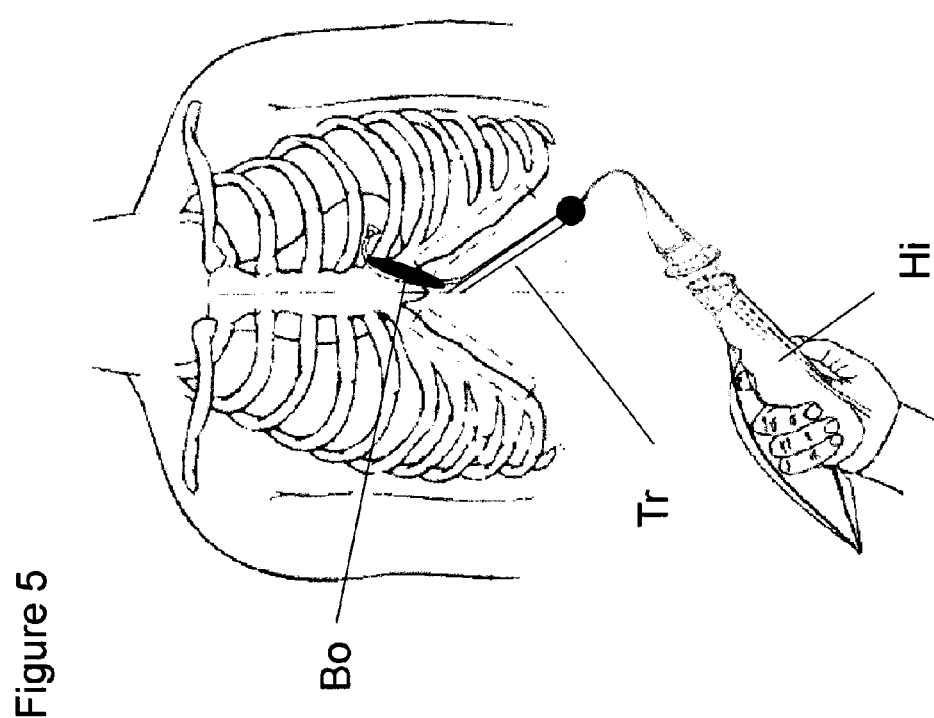
FIG. 5 is a schematic illustration of a subject (with some anatomic features revealed) and a haptic device as described and claimed herein during an initial phase of exemplary procedure.

The patient is brought to an operating room and is accordingly prepared per robust sterilization procedures and draped in the usual fashion. The recent median thoracotomy incision is depicted in FIG. 4. An initial incision of about one centimeter (1 cm) is made in the sub-xyphoid location and dissection is carried out to the subcutaneous tissues, though other techniques such as parasternal or limited thoracotomy approaches can be used as depicted in FIG. 4. In an emergency situation this can be performed at the patient's bedside or other convenient and accessible location. If the clinical picture is the result of traumatic injury the system is portable and can also be used in the field as described below. The blades 104, which are in the initial overlap position 136 (also denoted as "Bo" in FIG. 5), are inserted into the incision through a stiff medical introducer typically having an outer portion and an inner portion such as a trocar, which is a sharp-pointed surgical instrument used with a cannula to puncture a body cavity for access and optionally fluid aspiration 136 (denoted as "Tr" in FIG. 5) as illustrated in FIG. 5 and the control mechanism such as a handle 140 (e.g., an instrumented haptic glove or other haptic interface 100) is connected through trocar 136 to engage the blade mechanism and provide haptic feedback and user control. The trocar 136 is removed once the blade 104 and it associated structures and collapsible and expandable mechanism is in position and control over the end-effector 102 (including the blades 104, etc.) is maintained using the haptic handle interface 140 (denoted as "Hi" in FIG. 5), which can be an instrumented haptic glove, a haptic heart or a haptic handle or other haptic interface 100. Fluoroscopic or ultrasonic guidance can be used to assist but is not needed as the procedural process is palpable. The sensed mechanical data from the tactual tip sensors 106 (or "tt" in FIG. 1) peripherally located on the top inserted blade(s) 104 is palpated by the operator holding the haptic interface 140. If an instrumented haptic glove interface 100 or system is implemented (not depicted in FIG. 5), the tactile feedback is ideally provided at the distal portion of each haptic finger, i.e., in the same location (e.g. finger tips), providing the operator with a "real feel" extracardiac experience (true coupling). In one embodiment of according to the instant disclosure, the sensors 106 are composed of piezoelectric sensors. In this circumstance, the analog data is digitized via an A/D convertor in processor 200. Various types of haptic rendering as known by those experienced in the art can be implemented in processor 200. Other sensor designs including those designed with nanotechnology (i.e., using nanosensors, nanomaterials, nano-scale components, and the like) can be used as well.

Tactile feedback is generated at the haptic interface 100 as shown in FIG. 5, and provides the operator with tactile sensations which in more advanced embodiments (e.g., a haptic heart model having a compendium of instrumentation) provide sensations of compression, vibration, multi-dimensional force application, temperature variations, reproducing feelings of friction, stretch, slip, displacement, softness, deformation, stress, strain, shear (e.g., using a shear factor) and the like. Thus, as the tissues are dissected and at least one of the haptic finger blades 104 is inserted deeper into the body toward the cardiac epicardial and pericardial structures the operator appreciates the variations in resistance present in the subcutaneous tissues and fascial planes much as if the operator is doing blunt dissection with their own finger(s).

By way of example, haptic interface 100 can comprise a multi-fingered haptic interface that will provide high precision three dimensional force at the fingertips in a large workspace and optimally will have multiple degrees of freedom (e.g. 15 DOF). The workspace (i.e. relationship between sensor locations and haptic display volume) can be a default value that is constant, or change in volume depending on the nature of sensed signals (e.g. fine vs. coarse anatomic detail), location of the end-effector(s), vary based on operator command or as based on a programmed equation that is a function of a pre-defined set of variables, indices, parameters.

Figure 6:
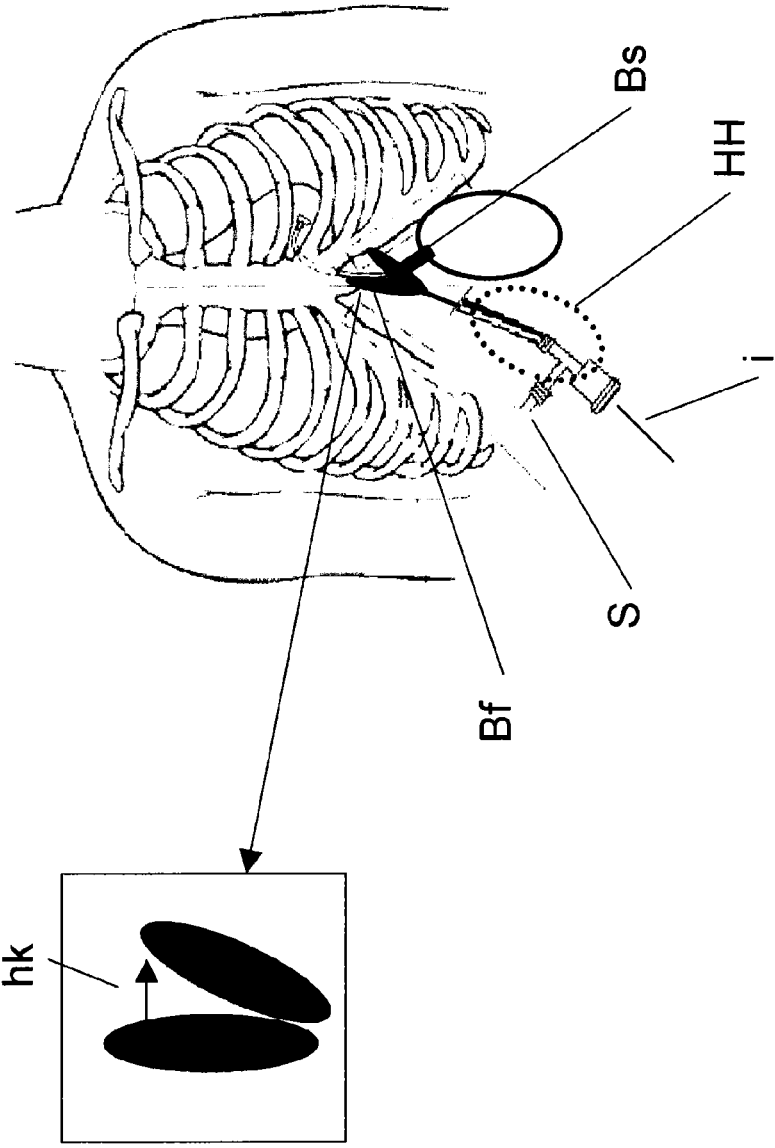
FIG. 6 is similar to FIG. 5 but illustrating a portion of a device as described herein engaging cardiac tissue of a patient (with FIG. 6 providing an illustration of the relative motion between a pair of opposing blade members to engage tissue).

Once the overlapping haptic finger blade(s) 104 enter the subcutaneous tissues the operator separates the digits or one or more fingers at the level of the haptic interface 100 and exposes one or more of the underlying blades 104 that assist in dissection (FIG. 6). As the initially overlapped blades 104 (in form of a single finger blade 104) enter the pericardial sac, suction can be initiated through a suction cannula 134 (also denoted as "S" in FIG. 6), that fluidly couples to the inserted instrument to a depository for fluid collection and analysis (not depicted) if needed. This suction cannula 134 can be used to aspirate the blood and other body fluid from within the pericardial space and can also be used for irrigation purposes. The suction due to applied vacuum or the fluid pumped for irrigation purposes can be provided continuously or intermittently, as desired. As the pericardial sac is contacted gentle probing will enable the blade(s) 104 to enter the pericardial space and the operator will oftentimes feel a "pop" or single vibrating sensation. This can be palpable at the haptic interface 100 using haptic rendering techniques. Haptic rendering may be utilized to simulate other static or dynamic tissue properties including but not limited to tissue texture, softness, elasticity, hardness, pulsations, vibrations and the like.

Figure 7:
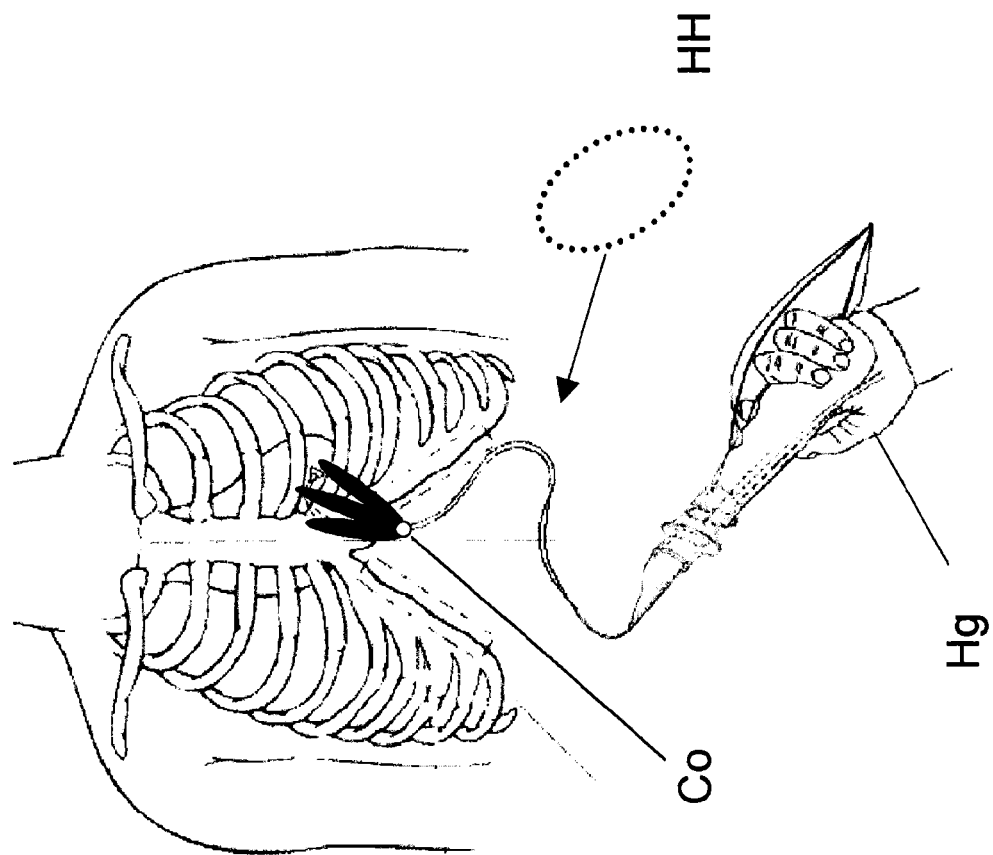
FIG. 7 is also similar to FIG. 5 (and FIG. 6) and illustrates another embodiment of a device and manual handle for operating an end-effector according to this disclosure.

Tactual data can be transmitted using analog (e.g., piezoelectric sensors) or digital electrical data (denoted as "d" in FIG. 1) and input into the processor 200, or in one embodiment, by air or liquid that is contained about one or more blades 104 through a pneumatic or hydraulic system. The pneumatic, (denoted as "p" in FIG. 2), or hydraulic, (denoted as "h" in FIG. 2), mechanisms (collectively denoted by 118 in FIG. 2) function simply by transmitting pressure that is exerted upon air or liquid material of specific viscosity surrounding one or more of the compressible blades 104 within each blade finger (see e.g., FIG. 2 and FIG. 7) to the operator at the haptic interface 100 which is depicted as a haptic heart model (denoted as "HH," a circle drawn in ghost in FIG. 6). This pressure is perceived at the level of the haptic interface, for example, by movement of the air or liquid about an instrumented haptic glove surrounding and operator's finger or alternatively with a haptic heart model, which is, in one embodiment herein, disposed in a continuum with the air or liquid contained within the hermetically sealed webbing material 110, which can comprise a volume of insulation located about one or more of the inserted blades 104.

The system can implement more than one type of haptic interface 100. Thus, in one embodiment, the instrumented haptic glove (denoted as "Hg" in FIG. 7) or a multi-fingered haptic interface is used to access the intra-thoracic space (with or without a haptic handle interface) and then a haptic heart model is exchanged and connected to the system at connector, Co in FIG. 3 and FIG. 7, for delivery of closed chest cardiac massage if needed. Compressive forces on the end-effector 102 (e.g., deformable blades 104 coupled about the heart) of the system are appreciated at the level of the haptic interface (HH in FIG. 7) and the forces applied to HH are imparted to the deformable blades for mechanical cardiac support.

By way of example, once the end-effector 102 (and portions of its related system components) is inserted and in the appropriate location the blade fingers are spread apart. Again, this is appreciated by the operator through the haptic interface (e.g., opening, closing, flexing three fingers of a sterile haptic glove) so that the dissection of tissues and fibrosis occurs safely and adhesions or fibrous tissues within the pericardial space are dissected free from other nearby tissue thus helping mobilize any loculated pericardial blood or fluid. This technique can also be applied for treatment of chronic constrictive pericarditis or to free up loculated pockets of organized pericardial fluid and thrombus.

The haptic blades 104 (which can be described as individual but connected finger-like structures) can be left about the heart and acquire additional sensor data that relates to the mechanical function of the heart. The operator then disconnects the multi-fingered haptic interface 140,100 and exchanges it with the haptic heart which is, as described herein as resilient, non-rigid, deformable and optionally equipped with various transducers or actuators, fluid passageways, pumps or vacuums and the like. The operator can manually palpate and appreciate the palpated action of the heart and motion with the haptic heart.

In one embodiment and as mentioned above, the haptic heart is oblong and can be held by the operator and capable of generating mechanical sensations simulating cardiac tissue motion. Its mechanical properties such as elasticity, mechanical recoil, twist, contraction, etc. are similar to human cardiac tissue. The pneumatic or hydraulic system enables the transmission of mechanical data and tactual feedback to the operator. Likewise, the operator can squeeze the Haptic Heart and generate mechanical support to the heart by displacing air or liquid within the pneumatic or hydraulic system, or by providing a signal, or surrogate, related to the desired impact upon the actual patient's heart via the end-effector 102. This can also be accomplished electronically using a haptic glove or multi-fingered haptic interface, by way of example. The amount of support needed can be determined qualitatively by the operator based on tactile feedback from the pneumatic or hydraulic system and/or from data acquired by the sensors on the inserted blades transmitted to the control system which receives the sensor data for processing and generating real time tactile feedback at the haptic interface 100.

Closed chest cardiac massage can be administered if needed. The mechanical support can be in one or more forms. Potentially optimal cardiac support can be achieved by having a plurality of the blades 104 (or finger-like structures) with webbing as illustrated in FIG. 1 apply adequate pressure on the heart and flexing about the cardiac surface. As noted previously webbing 110 between the blades 104 provides relatively even distribution of applied force to the myocardial substrate. The blades 104 can each have one or more joints or hinge mechanisms to provide relatively customized coupling and flexion and the blades 104 also can be fitted with a delivery system or systems for administering therapeutic agents or devices such as medications (e.g., via perforated or microporous membrane surfaces), as well as permanently implanted sensors and electrodes. In an embodiment, tactile feedback (e.g., proprioceptive, kinaesthetic) via sensor like mechanoreceptors gathers the needed data and reproduces the intra-cardiac "experience" through the haptic interface 100 (e.g., haptic glove and heart) for fine, detailed tactual information and augments the gross mechanical data provided via the hydraulic or pneumatic system reducing the likelihood of mechanical injury (e.g., cardiac contusion).

A gentle assist to cardiac contraction may be generated or more forceful contractions administered as needed similar to an acutely- or a chronically-implanted LVAD or other cardiac assist system. Torsion can be applied using torque arm, A, to simulate the natural twisting and untwisting of the heart under normal circumstances (illustrated to a degree in FIG. 2). The timing of force application at different segments of the end-effector 102 is determined mechanically and/or electrically as previously noted, with or without compensation for the physiologic time delay inherent between the cardiac mechanical response due to the passing of electrical wavefronts across and through the myocardial substrate. Different segments (joints formed into and/or size, shape, and rigidity of the blades 104) can generate varying amounts of supportive force upon the heart at different times normalizing synchronous cardiac mechanical function. This can be done manually or automatically whereby processor 200 and or control system 300 direct the timing, amplitude and frequency of the action of the end-effector 102. A closed feedback loop comprised of one or more sensors 106 (denoted as "PzS" in FIG. 1), the haptic interface 100, and the system processor 200, function as part of a control system 300, which provides for monitoring of cardiac function (e.g., CO, systemic perfusion, adequate or reasonably consistent blood pressure and heart rate) and determining the optimal programming of the assist device (e.g., temporal and spatial characteristics). Any number of inputs (e.g. three dimensional electromagnetic mapping system data, navigational system data, hemodynamic information, electrophysiologic data, imaging data, respiration monitor, cardiogenic impedance) can be input into 300 as auxiliary information, auxiliary data collection, and integrated into the analyzed data as to optimize functionality.

By way of example, a dysynchronous myopathic heart muscle will not generate adequate CO and different myocardial regions will contract and move in a dysynchronous pattern. This is detected electrically and/or mechanically by the end-effector 102 and its associated sensors 106 and corrected by the control system much as currently available pacemakers provide cardiac resynchronization therapy or LVAD provide support to a left ventricle. The system design herein provides this as mechanical support in a synchronous fashion so that myocardial segments that would ordinarily contract late in the cardiac cycle are stimulated electrically (e.g., via pacing electrodes on blade(s) 104) and/or mechanically via direct action of the blades 104 of the end-effector 102. For example, the laterally located portions of an end-effector of series of blades 104 can be controlled to flex earlier during the systolic ejection phase relative to more medially located blades 104 by some temporal index or preset window (e.g., 80 milliseconds).

Auxiliary input that is comprised of visual or auditory data will improve the operator's tactile sensing acuity and optimize true coupling through visual and auditory haptic responses.

If there is dysrhythmia, the electrode/conductive portions of the blades 104 can essentially provide sensor signals and haptic feedback to an operator to allow the operator to effectively diagnose the pathology underlying the dysrhythmia problem and deliver pacing stimuli as well as defibrillation therapy, if appropriate, along one or more therapy vectors (defined as lying substantially between electrodes of opposing polarity) with varying polarities. Thus, electrical and mechanical synchronization is provided to the failing heart.

Figure 8:
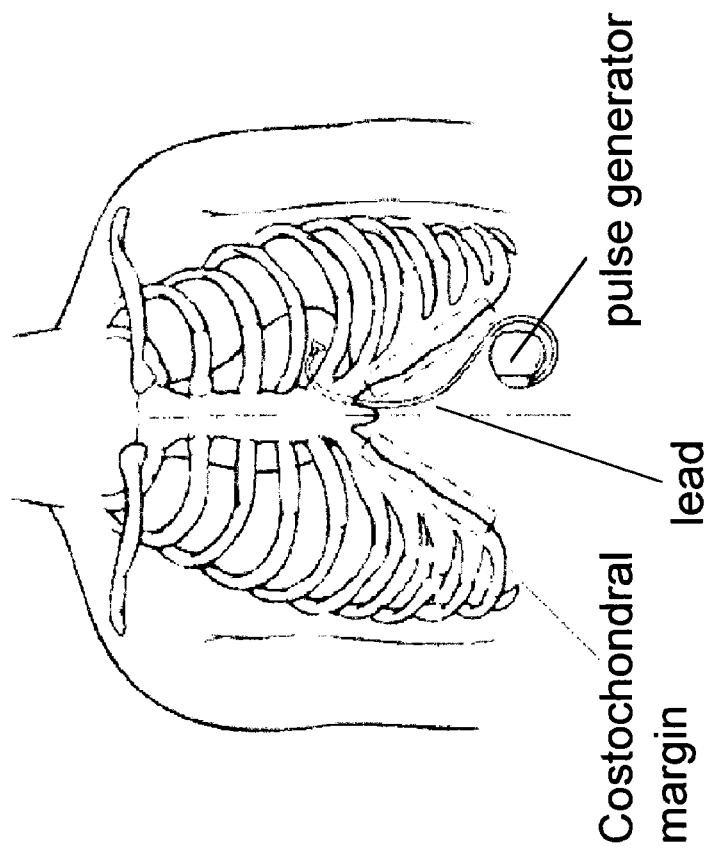
FIG. 8 schematically illustrates the implanted location of an implantable pulse generator (IPG) in an anterior abdominal left upper quadrant location adjacent the left costochondral margin of a subject following closed-chest, minimally invasive surgical (MIS) resuscitation according to this disclosure.

The system can run autonomously by gathering mechanical and electrical data and appropriately delivering the proper type of therapy as needed until the patient is stabilized. Control systems within 300 similar to those present in current pacing/defibrillator systems and cardiac assist devices are programmed or operated to provide the type of palliative or potentially curative therapy and the timing of therapy delivery during the cardiac cycle. Permanently implanted electrodes can be positioned about the heart as illustrated in FIG. 8 with the pulse generator implanted and connected to the electrode and lead system.

The system can also be configured to deliver therapy such as ablation of tissue, and provide various pharmacological and therapeutic agents such as anti-arrhythmic substances and stem cells or other biologic materials via the fluid pump(s), sources of reduced pressure, hydraulic or pneumatic systems. Thus resulting in haptic, or palpable, identification of pathologic tissue enabling an operator to promptly and accurately treat the appropriate regions and tissues of interest and even optimize surgical approaches in patients with anomalous anatomy (e.g., congenital heart disease) that require alternative methods for accessing cardiac structures.

The system can be teleoperated as to reduce the waiting time for and provide ready access to a team of experienced surgeons to treat critically ill patients at remote locations. As another clinical example the following should be considered:

Oftentimes in, on, or near a field of battle emergency thoracotomies are performed. The inventor hereof posits that the statistical survival rate is high relative to a closed chest (i.e., MIS) procedure. The blades 104 according to the disclosure can be composed in full or part of an energy harvesting material such as a Zinc Oxide composite or other material (e.g., piezoelectric or material incorporating conductive nanotubes, and the like) that can harvest the energy from diaphragmatic, skeletal and cardiac muscle motion of a patient and supply it to an attached, portable battery power pack. Capacitive elements coupled to the power pack ensure that a charge capable of defibrillation is always available and the stored and recharging energy supply can be used to have the system function as a portable assist unit that can be implanted in the field. The webbing material 110 and suction capabilities of the system can thus serve to seal and heal various wounds on or about the anatomy, including individual organs of the patient (e.g. re-expansion of a pneumothorax). Any perforations (e.g., due to bullet and/or shrapnel injuries) can be treated while an end-effector 102 is deployed. For example, the blades 104 and webbing 110 can contain bleeding and the hydraulic/pneumatic system (and contractile system for the end-effector(s)) can apply the appropriate amount of pressure during cardiac massage/compressions to mitigate bleeding or irrigate and cleanse contaminated tissue. Blood volumes can be measured via the suction apparatus using known components and relationships to fluid flow, for example. Low energy or intermittent suction can be used to also create a vacuum that opposes and attracts the end-effector 102 to tissue layers and simultaneously compresses any bleeding structures or re-expand a collapsed lung. The hydraulic/pneumatic system can also be used to deliver thrombotic agents to specific locations (although related lumens or tubing may require valves or switches to control reversal of fluid flow) or even recirculate any blood loss or other bodily fluid evacuated from damaged tissues via intravenous or intracardiac routes.

Another application of the teaching herein in an acute setting relates to use of electrodes disposed on one or more of the blades 104 of an end-effector 102 to electrically and/or mechanically cause diaphragm stimulation for patients with respiratory arrest. Such stimulation can be readily performed according to the foregoing MIS techniques as a sub-xyphoid entry typically occurs at the level of, or relatively near, the diaphragm muscle.

A commercial entity, known by the tradename "DuraAct" and also identified as "Physik Instrumente" of Germany provides piezoelectric material with energy harvesting properties that can harvest energy from moving structures such as the beating heart, diaphragmatic and skeletal muscles. It can be used to recharge and maintain a re-chargeable battery out in the field as a self-sustaining life-sustaining apparatus, among other possible advantages. Such commercially-available material(s) can readily be incorporated into portions of the webbing material 110 and/or the blades 104 and be machined to have a cutting edge, if desired.

Such energy harvesting properties can be implemented herein in a reciprocal configuration wherein the end-effector(s) include portions covered or including energy harvesting materials and the operator interface also includes portions covered or including same. Thus, when the operator squeezes or actuates the controller such as via a handle-type interface or via an instrumented haptic heart including materials such as piezo-actuator (e.g., DuraAct-containing coating adapted for a deformable soft tissue model) a voltage and electrical current signal is generated that triggers or activates the end-effector (e.g., DuraAct Blade composite) to massage and/or compress about the heart. The signal can be an amplified purely-analog current signal directly from the energy generated by the hand-held piezo-actuator or can trigger/activate via an analog-to-digital converter an electromechanical system that drives the inserted blades 104 of the end effector 102.

Thus both ends of the system have similar piezo actuators and are reciprocating. The deformation of the inserted DuraAct-coated or -containing blades 104 likewise can activate the haptic interface 100 (e.g., the haptic heart model, an instrumented haptic glove, or haptic handle and the like) as to generate the haptic effect(s) to the operator and thus convey that adequate contractility is present or if a gentle assist is needed or if a PEA condition is present and aggressive mechanical support is required. Squeezing the haptic heart/handle can also be used to harvest energy in the field if cardiac compressions or respiratory support is not needed.

The foregoing is not limited to the named DuraAct material as any piezoelectric material possessing energy harvesting properties and capable of serving as an actuator will store potential energy and deliver kinetic energy. When a current is delivered to the material it will contract. Thus, the blades 104 or other similar expandable and collapsible end-effector 102 can be used to harvest and store energy when there is normal cardiac contractility and/or diaphragm muscle contraction and then serve as an actuator deforming the blades 104 to contract and support myocardium and/or diaphragm muscle in time of need. The webbing 110 would thus act as a confining structure as to control the contraction of the webbing material 100 and the blades 104 (or equivalent structure of end-effector 102). Thus, the exterior portion of the webbing 110 (between the elongate ribs or blades 104) act to restrict motion and the undersurface (contacting the myocardium or diaphragm muscle of the pulmonary system) should be elastic so the force is applied radially inward. The properties of the blades 104 and webbing 110 can vary in direction or strength of contraction or between the expanded and partially expanded states according to need (e.g., configured to deliver compressive forces toward the pulmonary parenchyma) for respiratory support.

The foregoing text-based descriptions and scenarios are intended as illustrative and not limiting as to the various implementations and configurations for the family of cardiac and organ support modalities taught herein and should be considered as merely a partial illumination thereof.

EXAMPLES

The following examples are also intended as illustrative and in no manner limiting as to the scope and breadth of the foregoing description and the accompanying drawings to those of skill in the art.

1. A minimally invasive surgical (MIS) instrument configured to provide mechanical and electrical support and acquire sensor-based physiologic signals from an intrathoracic organ of a patient while providing haptic feedback to an operator, comprising:

an end-effector system adapted for transthoracic insertion into the patient and having a collapsed configuration for deployment and retraction and an expanded working configuration, wherein the working configuration provides a receiving location and in a partially-collapsed deployment configuration compresses a portion of the intrathoracic organ disposed in the receiving location;

a plurality of transducers coupled to the end-effector system, each transducer providing at least one output signal therefrom; and a haptic interface operably coupled to the plurality of transducers, said haptic interface including at least one processor configured to transform the respective output signals from the plurality of transducers into a haptic response that provides an operator of the MIS instrument with feedback that the operator utilizes to position the receiving location of the end-effector and monitor or adjust control of the end-effector.

1A. An MIS instrument according to claim 1, wherein the intrathoracic organ comprises one of a mammalian heart, lung and an innervated portion of diaphragm tissue.

1B. An MIS instrument according to example 1, wherein the end-effector system includes a plurality of at least a pair of elongate finger-like elements or elongate ribs.

1C. An MIS instrument according to example 1B, wherein at least a pair of adjacent finger elements of the end-effector system include a web of material therebetween.

1D. An MIS instrument according to example 1C, where the web of material comprises opposing sheets of material.

1E. An MIS instrument according to example 1D, wherein one of the opposing sheets of material and the web of material include a port for receiving a fluid.

1F. An MIS instrument according to example 1E, further comprising a control circuit configured to increase and decrease a volume of fluid disposed within one of the opposing sheets of the material and the web of material via the port.

1G. An MIS instrument according to example 1F, wherein the control circuit senses cardiac electrical activity and, in response, the control circuit one of: periodically increases and decreases the volume of fluid disposed within the opposing sheets and increases and decreases the pressure of the fluid disposed within the opposing sheets based at least in part upon the sensed cardiac electrical activity.

1H. An MIS instrument according to example 1 G, further comprising a physiologic delay circuit operable to one of temporally synchronize and temporally adjust an electrical cardiac signal with a mechanical cardiac signal.

2. A minimally invasive surgical (MIS) instrument and system providing haptic feedback for an operator and adapted for acute resuscitation of a mammalian subject, comprising:

an MIS-deployable end-effector having a fully-expandable state and a partially-expandable when deployed to a target of cardiovascular tissue and a compact, collapsible state when not deployed to the target of cardiovascular tissue, and adapted to at least partially encircle a portion of myocardium of a mammalian subject when disposed in both the fully-expandable state and the partially-expandable state;

a plurality of sensors coupled to the end-effector and the portion of myocardium each adapted to provide at least one output signals therefrom; and a processor coupled to the output signals and configured to transform the output signals and to convey the transformed signals to at least one of: a standard output interface, a haptic output interface, a haptic user interface, and an operator, wherein the transformed signals provide feedback for one of: initially positioning the end-effector and advantageously repositioning the end-effector, for optimal functioning of the end-effector.

2A. An MIS instrument according to example 2, wherein the haptic user interface comprises one of an elongate instrumented haptic handle and an instrumented haptic glove.

2B. An MIS instrument according to example 2A, wherein the haptic handle comprises at least one linear motor and at least one rotary motor, wherein the at least one linear motor is disposed at a center of gravity of said handle.

2C. An MIS instrument according to example 2, further comprising a fluid conduit coupled to the end-effector, wherein said fluid conduit comprises one of: a lumen closed at a distal end thereof and a lumen having at least one perforation formed in a distal portion thereof.

2D. An MIS instrument according to example 2, wherein the end-effector comprises a set of distinct spaced-apart flanges and a web portion couples adjacent flanges and said web portion comprises a series of pleated portions that collapse together into the compact, collapsible state.

2E. An MIS instrument according to example 2D, wherein the web portion encapsulates a portion of at least one of the spaced-apart flanges and wherein said spaced-apart flanges comprise at least one of an electrically conductive material and an energy-harvesting material.

2F. An MIS instrument according to claim 10, wherein at least two of the plurality of sensors comprise: a plurality of mechanical sensors, a body-fluid parameter sensor, at least two electrodes, an accelerometer, a blood oxygen sensor, a pressure sensor, a flow sensor, and a strain gauge.

2G. An MIS instrument according to example 2F, wherein the output signals include at least one cardiac mechanical signal and at least one cardiac electrical signal and said processor introduces a physiologic time delay to temporally synchronize the at least one electrical signal and the at least one mechanical signal.

2H. An MIS instrument according to example 2G, further comprising:

at least one actuator and wherein the processor couples to the actuator and provides a temporally synchronized output signal to a haptic interface, and wherein the haptic interface comprises one of: an instrumented haptic handle mechanism, an instrumented haptic glove, and a haptic heart and said haptic interface is coupled to the processor and adapted to receive the temporally synchronized output signal.

2I. An MIS instrument according to example 2H, further comprising a handle mechanism coupled to the processor adapted to receive the temporally synchronized output signal.

2J. An MIS instrument according to example 2I, wherein the handle mechanism couples to a remote source of energy.

2K. An MIS instrument according to example 2I, further comprising a chronically implanted pulse generator (IPG) coupled to the MIS instrument so that the operation of the MIS instrument and the operation of the IPG are coordinated.

3. A minimally invasive cardiorespiratory support (MICS) system, comprising:

an end-effector including at least a pair of spaced apart elongate members and adapted to provide mechanical and electrical support to one of: a mammalian heart to promote perfusion and an intrathoracic organ; and a plurality of physiologic sensors coupled to the end-effector and configured to acquire sensor-based physiologic signals from the mammalian heart or the intrathoracic organ while providing haptic feedback to an operator of the MICS system when the MICS system is surgically positioned and optionally advantageously repositioned while in communication with the mammalian heart or the intrathoracic organ via at least one minimally invasive surgical incision, wherein the MICS system includes a webbing material disposed between an adjacent pair of the at least two spaced apart elongate members.

3A. An MICS system according to example 3, further comprising means operatively coupled to the MICS system to perform at least one of the following functions:

provide tactile feedback from an end-effector portion of the MICS system to a proximal end of the MICS system;

provide force-based feedback from the end-effector portion of the MICS system to a proximal end of the MICS system;

provide kinesthetic-based feedback from the end-effector portion of the MICS system to a proximal end of the MICS system;

provide proprioceptive-based feedback from the end-effector portion of the MICS system to a proximal end of the MICS system;

aspirate fluid via a fluid passageway coupled to the end-effector portion of the MICS system to a proximal end of the MICS system;

provide one of cardiac pacing, diaphragm stimulation, and defibrillation therapy via the end-effector portion of the MICS system;

provide one of manual, semi-automatic, and automatic hemodynamic support via the end-effector portion of the MICS system;

provide at least one of cardiac electrical monitoring and cardiac mechanical monitoring from an end-effector portion of the MICS system to a proximal end of the MICS system;

administer at least one therapeutic agents from an end-effector portion of the MICS system; and permanently implant at least one stimulation electrode in communication with the heart.

4. An acute cardio-respiratory support apparatus or acute cardio-respiratory support field-kit, including a minimally invasive surgical (MIS) instrument and system providing haptic feedback for an operator and adapted for one of: performing an acute cardiac resuscitation procedure and performing an intrathoracic organ-supporting procedure for a subject, said apparatus or field-kit comprising:

an MIS-deployable end-effector having an fully- and a partially-expanded state and a compact, collapsible deployment state adapted to at least partially encircle a portion of an intrathoracic organ of a subject when disposed in the fully-expanded state;

a plurality of sensors coupled to the end-effector and adapted to provide output signals therefrom;

a source of electrical potential adapted to couple to the end-effector; and a processor coupled to the source of electrical potential and configured to receive the output signals and adapted to transform the signals and to convey the transformed signals to at least one of: a standard output interface, a haptic output interface, a haptic user interface, a wireless interface, and an operator.

4A. An apparatus or field-kit according to example 4, wherein at least a portion of the end-effector includes an energy-harvesting material.

4B. An apparatus or field-kit according to example 4, wherein the source of electrical potential includes at least one of: a rechargeable battery cell, a non-rechargeable battery cell, a hard-wired grid-source of remote electrical potential, and a fuel cell.

4C. An apparatus or field-kit according to example 4, wherein the rechargeable battery couples to the energy-harvesting material.

4D. An apparatus or field-kit according to example 4D, further comprising:

at least one capacitive element coupled to one of: the rechargeable battery and at least one high-rate battery; and at least one high-power density electrode coupled to the at least one capacitive element and adapted to electrically communicate with myocardial tissue when the at least one capacitive element therapeutically discharges.

4E. An apparatus or field-kit according to example 4E, wherein the capacitive element comprises at least one super capacitor element.

4F. An apparatus or field-kit according to example 4, further comprising:

at least one fluid passageway fluidly coupled at a distal end to a perforated vessel formed within the end-effector via at least one fluid port and fluidly coupled at a proximal end to at least one of a fluid pump and a source of reduced pressure adapted to feed fluid to the end-effector and to one of: withdraw material from the end-effector and vacuum-adhere the end-effector to adjacent tissue, respectively; and valve means adapted for selecting an active channel for the fluid pump and the source of reduced pressure.

4G. An apparatus or field-kit according to example 4F, wherein the fluid pump couples to a reservoir and said reservoir is adapted to store at least one of: a pharmacological agent, a therapeutic agent, an anti-arrhythmic substance, a volume of stem cell tissue, a volume of biocompatible saline, recirculated blood or other body fluid and an anti-thrombotic agent.

4H. An apparatus or field-kit according to example 4F, wherein the at least one fluid passageway comprises at least one fluid passageway for each of the fluid pump and the source of reduced pressure.

4I. An apparatus or field-kit according to example 4F, further comprising a fluid measurement instrument coupled to an output of the source of reduced pressure wherein said instrument provides an output signal indicative of at least one of: a fluid volume passing therethrough and a fluid pressure parameter.

4J. An apparatus or field-kit according to example 4, wherein the energy-harvesting material comprises one of: a zinc oxide material, a conductive nano-scale material, piezo-electrical material, and a magneto-resistive material.

4K. An apparatus or field-kit according to example 4, further comprising a portion of elastic webbing disposed between at least a pair of elongate elements of said end-effector so that the organ is mechanically supported by the portion of elastic webbing in both the fully- and partially-expanded state.

4L. An apparatus or field-kit according to any of examples 4 to 4K, further comprising a non-transient computer readable medium coupled to the processor that includes at least two predetermined procedural instructions for use for at least two medical protocols that include use of the end-effector.

4M. An apparatus or field-kit according to example 4L, wherein one of the processor and the non-transient computer-readable medium includes at least one non-volatile memory storage location adapted to store information relating to at least one of: a usage continuum of the apparatus or field-kit over a temporal period and a usage relative to a specific patient.

4N. An apparatus or field-kit according to any of examples 4 to 4M, further comprising a sterile packaging surrounding all components of said apparatus or field-kit and including at least one indicia of one of: a tampering event, a use-by date, an instructions-for-use legend, and a package-shock event exceeding a preset threshold.

4O. An apparatus or field-kit according to example 4, further comprising at least a pair of electrodes disposed on one of: a portion of the end-effector and an extension of the end-effector, wherein at least one of said electrodes is configured to contact a portion of diaphragm tissue.

4P. An apparatus or field-kit according to example 4, wherein the end-effector is configured as at least three spaced-apart elongate fingers and wherein a webbing material at least partially couples adjacent elongate fingers together.

4Q. A method utilizing an apparatus or field-kit according to example 4, comprising:

creating a minimally-invasive surgical (MIS) incision in a portion of a thorax and optionally also in a portion of the pericardium of a subject;

advancing a distal end of the end-effector in the collapsed state through the MIS incision in the thorax and if the optional pericardial incision was created also through the MIS incision in the pericardium;

expanding the end-effector to one of the partially- and the fully-expanded state so that the end-effector mechanically engages a portion of the heart; and periodically actuating the end-effector so that it transitions between the partially- and the fully-expanded state to promote pulsatile blood flow within the heart.

4R. A method according to example 4Q, further comprising:
gathering physiologic signals and data about the heart via the sensors;
conveying the signals and data to one of: a user interface, a haptic user interface, a controller for the end-effector, a robotic controller coupled to the end-effector.

4S. A method according to example 4Q, further comprising:
harvesting energy from an energy-converting material disposed on portions of the end-effector; and
conveying the harvested energy to an energy storage unit.

Of course, numerous modifications may be made utilizing the foregoing teaching to the advantage of diverse mammalian populations without departing from its scope as defined in the appended claims.

I claim:

1. A minimally invasive surgical (MIS) instrument configured to provide mechanical and electrical support and acquire sensor-based physiologic signals from an intrathoracic organ of a patient while providing haptic feedback to an operator, comprising:
    an end-effector system adapted for transthoracic insertion into the patient and having a collapsed configuration for deployment and retraction, an expanded working configuration wherein the expanded working configuration provides a receiving location, and a partially-collapsed deployment configuration that compresses a portion of the intrathoracic organ disposed in the receiving location;
    a plurality of transducers coupled to the end-effector system, each transducer providing at least one output signal therefrom;
    a haptic interface operably coupled to the plurality of transducers, said haptic interface including at least one processor configured to transform the output signals from the plurality of transducers into a haptic response that provides the operator with feedback that the operator utilizes to position the receiving location of the end-effector system and monitor or adjust control of the end-effector system; and
    a control circuit configured to increase and decrease a volume of fluid in the end-effector system, wherein the control circuit senses electrical or mechanical activity of a heart or a lung as sensed activity and, in response, the control circuit periodically increases and decreases the volume or pressure of fluid disposed within the end-effector system based at least in part upon the sensed activity.

2. A MIS instrument according to claim 1, wherein the intrathoracic organ comprises one of a mammalian heart, a portion of lung tissue, and an innervated portion of diaphragm tissue.

3. A MIS instrument according to claim 1, wherein the end-effector system includes a pair of elongate finger-like elements or elongate ribs.

4. A MIS instrument according to claim 3, wherein the pair of elongate finger-like elements or elongate ribs are adjacent one another and include a web of material therebetween.

5. A MIS instrument according to claim 4, wherein the web of material comprises opposing sheets of material.

6. A MIS instrument according to claim 5, wherein the web of material includes a port for receiving a fluid.

7. A minimally invasive surgical (MIS) instrument configured to provide mechanical and electrical support and acquire sensor-based physiologic signals from an intrathoracic organ of a patient while providing haptic feedback to an operator, comprising:
    an end-effector system adapted for transthoracic insertion into the patient and having a collapsed configuration for deployment and retraction, an expanded working configuration wherein the expanded working configuration provides a receiving location, and a partially-collapsed deployment configuration that compresses a portion of the intrathoracic organ disposed in the receiving location;
    a plurality of transducers coupled to the end-effector system, each transducer providing at least one output signal therefrom;
    a haptic interface operably coupled to the plurality of transducers, said haptic interface including at least one processor configured to transform the output signals from the plurality of transducers into a haptic response that provides the operator with feedback that the operator utilizes to position the receiving location of the end-effector system and monitor or adjust control of the end-effector system;
    wherein the end-effector system includes a pair of elongate finger-like elements or elongate ribs that are adjacent one another and include a web of material therebetween, the web of material comprising opposing sheets of material and includes a port for receiving a fluid; and
    a control circuit configured to increase and decrease a volume of fluid disposed within the web of material via the port, wherein the control circuit senses electrical or mechanical activity of a heart or a lung as sensed activity and, in response, the control circuit periodically increases and decreases the volume of fluid disposed within the opposing sheets or increases and decreases the pressure of the fluid disposed within the opposing sheets based at least in part upon the sensed activity.

8. A MIS instrument according to claim 7, further comprising a physiologic delay circuit operable to temporally synchronize or temporally adjust an electrical cardiac signal with a mechanical cardiac signal.

* * * * *